United States Patent [19]
Ecker et al.

[11] Patent Number: 5,736,294
[45] Date of Patent: Apr. 7, 1998

[54] REAGENTS AND METHODS FOR MODULATING GENE EXPRESSION THROUGH RNA MIMICRY

[75] Inventors: David J. Ecker, Leucadia; Thomas W. Bruice, Carlsbad; Timothy A. Vickers, Oceanside, all of Calif.

[73] Assignee: ISIS Pharmaceuticals, Inc., Carlsbad, Calif.

[21] Appl. No.: 724,500

[22] Filed: Jun. 27, 1991

Related U.S. Application Data

[63] Continuation-in-part of Ser. No. 497,090, Mar. 21, 1990, abandoned.

[51] Int. Cl.$^6$ .................... C12N 5/08; C07H 21/02
[52] U.S. Cl. ........................ 435/240.2; 536/24.5
[58] Field of Search ................ 435/5, 6, 7.1, 172.1, 435/240.2; 536/23.1, 24.1, 24.5

[56] References Cited

FOREIGN PATENT DOCUMENTS

| | | |
|---|---|---|
| A-0 331939 | 9/1989 | European Pat. Off. |
| WO-A-9 111535 | 8/1991 | WIPO |
| WO A-9 202228 | 2/1992 | WIPO |
| WO A-9 205195 | 4/1992 | WIPO |

OTHER PUBLICATIONS

Hawley-Nelson et al. "The Specific DNA Recognition Sequence of the Bovine Papillomavirus E2 Protein is an E2-Dependent Enhancer", EMBO Journal, vol. 7, No. 2, pp. 525–531, 1988.
P.S. Sarin et al., "Inhibition of Acquired Immunodeficiency Syndrome Virus by Oligonucleoside Methylphosphonates", Proc. Natl. Acad. Sci., Oct. 1988, vol. 85, No. 20, pp. 7448–7451.
J. Liszieiwics et al., "Repression of the TAT Function Through Multiple TAR RNA Sequences", J. Cell. Biochemistry, 1990, vol. 14D, p. 123.
Agrawal et al., Proc. Natl. Acad. Sci. USA 86:7790 (1989).
Berkhout, Cell 59:273 (1989).
Buck et al., Science 248:208 (1990).
Casey et al., Science 240:924 (1988).
Dayton et al., Science 246:1625 (1989).
Dayton et al., J. Acq. Immune Deficiency Syndromes, 1:441 (1988).
Ensoli et al., Nature, 345:84–86 (1990).
Feng, E.C. Holland, Nature 334:165 (1988).
Felber B.K. and Pavlakis G.N. (Science, 239:184–187 (1988).
Garcia et al., EMBO J. 8:765 (1989).
Graham et al., Proc. Natl. Acad. Sci. USA 87:5817–5821 (1990).
Haseltine, F. Wong-Staal, Scientific American, 259:52 (1988).
Henthorn et al., Proc. Natl. Acad. Sci. USA 85:6342 (1988).
Iyer et al., J. Am. Chem. Soc. (1990) 112:1253–1254.
Knapp, Methods Enzymol. 180:192 (1989).
Laspia et al., Cell 59:283 (1989).
Larson, B.H. Sells, Mol. Cell. Biochem. 74:5 (1987).
Le et al., Nucl. Acids Res. 16:5153 (1988).
Letsinger et al., Proc. Natl. Acad. Sci. USA 86:6553 (1989).
Malter, Science 246:664 (1989).
Matsukura et al., Proc Natl. Acad. Sci. USA, 84:7706 (1987).
Mori et al., Nucleic Acids Res. 17:8207 (1989).
Ratner et al., Nature 313:277 (1985).
Resnekov et al., J. Biol. Chem. 264:9953 (1989).
Sarin et al., Proc. Natl. Acad. Sci. USA 85:7448 (1988).
Shibahara et al., Nucl. Acids Res. 17:239 (1989).
Stevenson, P.L. Iversen, J. Gen. Virol. 70:2673 (1989).
Sharp, and R.A. Marciniak, Cell 59:229 (1989).
Sabatier et al., J. Virol., 65:961–967 (1991).
Salahuddin et al., Science, 242:430–433 (1988).
Tom, Hawaii Med. J., 48:131–134 (1989).
Tinoco et al., Cold Spring Harb. Symp. Quant. Biol. 52:135 (1987).
Tuerk et al., Proc. Natl. Acad. Sci. U. S. A. 85:1364 (1988).
Vogel et al., Nature, 335:606–611 (1988).
Viscidi et al., Science, 246:1606–1608 (1989).
Zuker, Science, 244:48 (1989).

Primary Examiner—David Guzo
Attorney, Agent, or Firm—Woodcock Washburn Kurtz Mackiewicz & Norris

[57] ABSTRACT

Expression of genes may be modulated by employment of compositions which are capable of RNA mimicry. A portion of RNA coded by the gene whose expression is to be modulated is selected which is capable of interacting with one or more proteins. An oligonucleotide or oligonucleotide analog is then prepared in such a way as to mimic the portion of the RNA. Cells containing the gene are then contacted with the oligonucleotide or oligonucleotide analog to effect the modulation. Therapeutic compositions and methods, especially for the treatment of human immunodeficiency, are disclosed.

14 Claims, 8 Drawing Sheets

5'  3'
GGGU<u>C</u>UCUCUGGUUAG<u>A</u>CCAGA<u>UC</u>UGAGC<u>CUGG</u>GAGCUCUCUGGCUAACUAGGGAACCC

FIG. IA

```
            C         A     UCU    CU
5'-GGGU UCUCUGGUUAG CCAGA    GAGC    G
3'-CCCA AGGGAUCAAUC GGUCU    CUGG    G
        -           -        ---    AG
```

FIG. IB

[7357]
UCCUUGGGUU CUUGGGAGCA GCAGGAAGCA CUAUGGGCGC AGCGUCAAUG
ACGCUGACGG UACAGGCCAG ACAAUUAUUG UCUGGUAUAG UGCAGCAGCA
GAACAAUUUG CUGAGGGCUA UUGAGGCGCA ACAGCAUCUG UUGCAACUCA
CAGUCUGGGG CAUCAAGCAG CUCCAGGCAA GAAUCCUGGC UGUGGAAAGA
UACCUAAAGG AUCAACAGCU CCUAGGGAUU UGGGGUUGCU CUGGAAAACU
CAUUUGCACC ACUGCUGUGC
                [7627]

FIG. 2

STABILITY OF 2'-DEOXY OR 2'-O-METHYL
OLIGONUCLEOTIDES IN HeLa CELL NUCLEAR EXTRACT

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
      ( A ) LENGTH: 59 base pairs
      ( B ) TYPE: nucleic acid
      ( C ) STRANDEDNESS: single
      ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:1:

```
GGGUCUCUCU GGUUAGACCA GAUCUGAGCC UGGGAGCUCU CUGGCUAACU    50

AGGGAACCC                                                  59
```

( 2 ) INFORMATION FOR SEQ ID NO:2:

( i ) SEQUENCE CHARACTERISTICS:
      ( A ) LENGTH: 40 base pairs
      ( B ) TYPE: nucleic acid
      ( C ) STRANDEDNESS: single
      ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:2:

```
GGUUAGACCA GAUCUGAGCC UGGGAGCUCU CUGGCUAACU               40
```

( 2 ) INFORMATION FOR SEQ ID NO:3:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:3:

```
GCCAGAUCUG AGC                                            13
```

( 2 ) INFORMATION FOR SEQ ID NO:4:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:4:

GCUCUCUGGC                     10

( 2 ) INFORMATION FOR SEQ ID NO:5:

( i ) SEQUENCE CHARACTERISTICS:
      ( A ) LENGTH: 29 base pairs
      ( B ) TYPE: nucleic acid
      ( C ) STRANDEDNESS: single
      ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:5:

GCCAGAUCUG AGCCUGGGAG CUCUCUGGC          29

( 2 ) INFORMATION FOR SEQ ID NO:6:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:6:

AATAGCACTC ACTATAGGGT CTCTCTGGTT AGACCA     36

( 2 ) INFORMATION FOR SEQ ID NO:7:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:7:

CCAGCATGTC TGGAGGGCAG                20

( 2 ) INFORMATION FOR SEQ ID NO:8:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:8:

GCCAGAGAGC CUUUGGGCUC UCUGGC             26

( 2 ) INFORMATION FOR SEQ ID NO:9:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:9:

GCCAGAGAGC CUGGGAGCUC CCUGGC        26

( 2 ) INFORMATION FOR SEQ ID NO:10:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:10:

UCUGAGCCUG GGAGCUCUCU        20

( 2 ) INFORMATION FOR SEQ ID NO:11:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:11:

CCAGAUCUGA GCCUGGGAGC UCUCUGG        27

( 2 ) INFORMATION FOR SEQ ID NO:12:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:12:

GAGCCUGGGA GCUC        14

( 2 ) INFORMATION FOR SEQ ID NO:13:

( i ) SEQUENCE CHARACTERISTICS:
    ( A ) LENGTH: 6 base pairs
    ( B ) TYPE: nucleic acid
    ( C ) STRANDEDNESS: single
    ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:13:

CUGGGA     6

( 2 ) INFORMATION FOR SEQ ID NO:14:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:14:

UCUGAGCCUG GGAGCUCU     18

( 2 ) INFORMATION FOR SEQ ID NO:15:

( i ) SEQUENCE CHARACTERISTICS:
    ( A ) LENGTH: 58 base pairs
    ( B ) TYPE: nucleic acid
    ( C ) STRANDEDNESS: single
    ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:15:

GGGUCUCUCU GGUUAGACCA GAUCUGAGCC UGGGAGCUCU CUGGCUAACU     50

AGGGAACC     58

( 2 ) INFORMATION FOR SEQ ID NO:16:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:16:

UCUGAGCCUG GGAGCUCUCU GGCUAACUAG GG     32

( 2 ) INFORMATION FOR SEQ ID NO:17:

( i ) SEQUENCE CHARACTERISTICS:
    ( A ) LENGTH: 17 base pairs (B) TYPE: nucleic acid
(C) STRANDEDNESS: single
(D) TOPOLOGY: linear (ii) MOLECULE TYPE: Other nucleic acid (iii) HYPOTHETICAL: NO (iv) ANTI-SENSE: NO (xi) SEQUENCE DESCRIPTION: SEQ ID NO:17:

```
UCUCUGGCUA ACUAGGG                                             17
```

(2) INFORMATION FOR SEQ ID NO:18:

(i) SEQUENCE CHARACTERISTICS:
  (A) LENGTH: 25 base pairs
  (B) TYPE: nucleic acid
  (C) STRANDEDNESS: single
  (D) TOPOLOGY: linear (ii) MOLECULE TYPE: Other nucleic acid (iii) HYPOTHETICAL: NO (iv) ANTI-SENSE: NO (xi) SEQUENCE DESCRIPTION: SEQ ID NO:18:

```
GGGUCUCUCU GGUUAGACCA GAUCU                                    25
```

(2) INFORMATION FOR SEQ ID NO:19:

(i) SEQUENCE CHARACTERISTICS:
  (A) LENGTH: 12 base pairs
  (B) TYPE: nucleic acid
  (C) STRANDEDNESS: single
  (D) TOPOLOGY: linear (ii) MOLECULE TYPE: Other nucleic acid (iii) HYPOTHETICAL: NO (iv) ANTI-SENSE: NO (xi) SEQUENCE DESCRIPTION: SEQ ID NO:19:

```
AGCUCCCAGG CT                                                  12
```

(2) INFORMATION FOR SEQ ID NO:20:

(i) SEQUENCE CHARACTERISTICS:
  (A) LENGTH: 12 base pairs
  (B) TYPE: nucleic acid
  (C) STRANDEDNESS: single
  (D) TOPOLOGY: linear (ii) MOLECULE TYPE: Other nucleic acid (iii) HYPOTHETICAL: NO (iv) ANTI-SENSE: NO (xi) SEQUENCE DESCRIPTION: SEQ ID NO:20:

```
AGCTCCCAGG CT                                                  12
```

(2) INFORMATION FOR SEQ ID NO:21:

(i) SEQUENCE CHARACTERISTICS:
  (A) LENGTH: 25
  (B) TYPE: amino acid
  (D) TOPOLOGY: linear (ii) MOLECULE TYPE: peptide (iii) HYPOTHETICAL: NO (v) FRAGMENT TYPE: internal fragment (xi) SEQUENCE DESCRIPTION: SEQ ID NO:21:

```
Gly Arg Lys Lys Arg Arg Gln Arg Arg Arg Pro Pro Gln Gly Ser
1               5                   10                  15
Gln Thr His Gln Val Ser Leu Ser Lys Gln
                20                  25
```

(2) INFORMATION FOR SEQ ID NO:22:

(i) SEQUENCE CHARACTERISTICS:
        (A) LENGTH: 37
        (B) TYPE: amino acid
        (D) TOPOLOGY: linear (ii) MOLECULE TYPE: peptide (iii) HYPOTHETICAL: NO (v) FRAGMENT TYPE: internal fragment (xi) SEQUENCE DESCRIPTION: SEQ ID NO:22:

```
Lys Lys Arg Arg Gln Arg Arg Arg Pro Pro Gln Gly Ser Gln Thr
1               5                   10                  15
His Gln Val Ser Leu Ser Lys Gln Pro Thr Ser Gln Ser Arg Gly
                20                  25                  30
Asp Pro Thr Gly Pro Lys Glu
                35
```

(2) INFORMATION FOR SEQ ID NO:23:

(i) SEQUENCE CHARACTERISTICS:
        (A) LENGTH: 17
        (B) TYPE: Nucleic Acid
        (C) STRANDEDNESS: Single
        (D) TOPOLOGY: Linear (ii) MOLECULE TYPE: Other Nucleic Acid (iii) HYPOTHETICAL: No (iv) ANTI-SENSE: No (xi) SEQUENCE DESCRIPTION: SEQ ID NO:23:

```
UCU GAG CCU GGG AGC UC                                    17
```

REAGENTS AND METHODS FOR MODULATING GENE EXPRESSION THROUGH RNA MIMICRY

This is 371 of PCT/US91/01822, filed Mar. 19, 1991 and a continuation-in-part of application Ser. No. 497,090, filed Mar. 21, 1990 now abandoned.

FIELD OF THE INVENTION

This invention relates to the field of therapeutics, particularly for infections, in animals and humans. It relates to the design, synthesis and application of oligonucleotide analogs which mimic the RNA secondary structures found in diseased cells, particularly cells infected with viruses and retroviruses. These mimics of the infectious RNA structures have been found to be able to modulate such infections.

BACKGROUND OF THE INVENTION

The biological function of RNA is mediated by its structure. mRNA is generally thought of as a linear molecule which contains the information for directing protein synthesis within the sequence of ribonucleotides. Recently, studies have revealed a number of secondary and tertiary structures in mRNA which are important for its function (See; I. Tinoco, P. W. Davis, C. C. Hardin, J. D. Puglisi, G. T. Walker, *Cold Spring Harb. Symp. Quant. Biol.* 52, 135 (1987). Secondary structural elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex, three dimensional structure.

Very little is known about the precise three dimensional structure of RNA. However, there have recently been a number of research efforts which have shown that RNA structures, including single stranded, secondary, and tertiary structures, have important biological functions beyond simply encoding information to make proteins in linear sequences. Some of these correlations have been discussed in: I. Tinoco, P. W. Davis, C. C. Hardin, J. D. Puglisi, G. T. Walker, *Cold Spring Harb. Symp. Quant. Biol.* 52, 135 (1987); O. Resnekov, M. Kessler, Y. Aloni, *J. Biol. Chem.* 264, 9953 (1989); C. Tuerk, P. Gauss, C. Thermes, et al., *Proc. Natl. Acad. Sci. U.S.A.* 85, 1364 (1988); D. E. Larson, B. H. Sells, *Mol. Cell. Biochem.* 74, 5 (1987); and G. Knapp, *Methods Enzymol.* 180, 192 (1989).

Oligonucleotides have been evaluated for effect on HIV. Agrawal and coworkers have used oligonucleotide analogs targeted to the splice donor/acceptor site to inhibit HIV infection in early infected and chronically infected cells. S. Agrawal, T. Ikeuchi, D. Sun, P. S. Sarin, A. Konopka, J. Maizel, *Proc. Natl. Acad. Sci. USA* 86:7790 (1989). Sarin and coworkers have also used chemically modified oligonucleotide analogs targeted to the cap and splice donor/acceptor sites. P. S. Sarin, S. Agrawal, M. P. Civerira, J. Goodchild, T. Ikeuchi, P. C. Zamecnik, *Proc. Natl. Acad. Sci. USA* 85:7448 (1988). Zaia and coworkers have also used an oligonucleotide analog targeted to a splice acceptor site to inhibit HIV. Zaia, J. A., J. J. Rossi, G. J. Murakawa, P. A. Spallone, D. A. Stephens, B. E. Kaplan, *J. Virol.* 62:3914 (1988). Matsukura and coworkers have synthesized oligonucleotide analogs targeted to the initiation of translation of the rev gene mRNA. M. Matsukura, K. Shinozuka, G. Zon, et al., *Proc. Natl. Acad. Sci. USA*, 84:7706 (1987); R. L. Letsinger, G. R. Zhang, D. K. Sun, T. Ikeuchi, P. S. Sarin, *Proc. Natl. Acad. Sci. USA* 86:6553 (1989). Mori and coworkers have used a different oligonucleotide analog targeted to the same region as Matsukura et al., K. Mori, C. Boiziau, C. Cazenave et al., *Nucleic Acids Res.* 17:8207 (1989). Shibahara and coworkers have used oligonucleotide analogs targeted to a splice acceptor site as well as the reverse transcriptase primer binding site. S. Shibahara, S. Mukai, H. Morisawa, H. Nakashima, S. Kobayashi, N. Yamamoto, *Nucl. Acids Res.* 17:239 (1989). Letsinger and coworkers have synthesized and tested oligonucleotide analogs with conjugated cholesterol targeted to a splice site. K. Mori, C. Boiziau, C. Cazenave, et al., *Nucleic Acids Res.* 17:8207 (1989). Stevenson and Iversen have conjugated polylysine to oligonucleotide analogs targeted to the splice donor and the 5'-end of the first exon of the tat gene. M. Stevenson, P. L. Iversen, *J. Gen. Virol.* 70:2673 (1989). Buck et al. described the use of phosphate-methylated DNA oligonucleotides targeted to HIV mRNA and DNA. H. M. Buck, L. H. Koole, M. H. P. Van Genderen, L. Smith, J. L. M. C. Geelen, S. Jurriaans and J. Goudsmit, *Science* 248:208 (1990). Each of these publications have reported some degree of success in inhibiting some function of the HIV virus. While each of these references is distinct from the approach of the present invention, each supports the view that nucleotide therapeutics in HIV infection is rational and based upon sound scientific principles. In each of these references the approach has been to design antisense oligonucleotides complementary to some portion of the HIV mRNA. The present invention relates to oligonucleotides which mimic an RNA and bind to a protein, rather than oligonucleotides which bind to the HIV RNA.

Heretofore, there have been no suggestions in the art of methods or materials which could be useful for mimicking the secondary or tertiary structures of RNA in order to modulate the expression of genes or to treat disease. This is despite the long-felt need for methods of therapeutics and for methods of inhibiting gene expression which may be related to diseases or disease states in animals. Accordingly, there remains a long-felt need for therapeutic materials and methods, especially for viruses and retroviruses.

OBJECTS OF THE INVENTION

It is a principal object of the invention to provide compositions and therapies for human diseases, particularly viral and retroviral infections.

It is a further object of the invention to provide therapeutic compositions which mimic the structure of a natural RNA.

Yet another object of this invention is to modulate gene expression in cells.

Yet another object of this invention is to provide therapies for human immunodeficiency virus infection.

These and other objects of this invention will become apparent from a review of the instant specification.

SUMMARY OF THE INVENTION

It has now been discovered that expression of genes may be modulated through the employment of compositions which are capable of RNA mimicry. The use of such RNA mimics can interfere with gene expression and, when that expression is implicated in the etiology of disease, lead to methods of therapeutics. In accordance with this invention, it has now been found that certain portions of RNA coded by genomic material can have secondary and even tertiary structure which plays a significant role in gens expression. It has now been found that the interaction of certain RNA's, especially messenger RNA's having secondary or tertiary structures, with proteins may be inhibited through the employment of oligonucleotides or oligonucleotide analogs which mimic at least a portion of the RNA. Such mimicry can interfere with the protein-RNA interaction and, through such interference, interfere with gene expression and the maintenance of disease states.

In accordance with preferred embodiments of the present invention, methods for modulating expression of a gene are provided comprising selecting a portion of RNA coded by the gene, which RNA is capable of interacting with one or more proteins. An oligonucleotide or oligonucleotide analog is then prepared in such a way as to mimic said portion of the RNA. Cells containing the gene are then contacted with the oligonucleotide or oligonucleotide analog to effect such modulation of expression. It will generally be the case that the gene is of an infectious organism, such as a virus or retrovirus. Preferably, the gene is from human immunodeficiency virus.

In accordance with other preferred embodiments, the protein is produced by a second portion of RNA coded by the infectious organism such as a virus or retrovirus. In such a case, the interaction of the protein with the RNA portion selected, if permitted to occur, would generally effect stimulation of expression of the gene such that inhibition of this interaction effects repression or modulation of gene expression.

It is preferred that oligonucleotides or oligonucleotide analogs of the invention mimic at least about 6 nucleotide units of the selected RNA. It is still more preferred that from 8 to about 60 nucleotide units be mimicked. From about 10 to about 30 nucleotide units are presently believed to be most preferred. In accordance with other preferred embodiments, the degree of mimicry of the selected RNA is such as to permit the oligonucleotide or oligonucleotide analog to achieve at least a portion of the secondary structure of the RNA.

In accordance with other preferred embodiments of the present invention, the TAR region, the CAR region, or the GAG-POL region of human immunodeficiency virus messenger RNA is targeted for oligonucleotide mimicry. The oligonucleotide or oligonucleotide analog is selected to be sufficient in its degree of mimicry as to be effective in interfering with the interaction of protein with the selected messenger RNA portions. Thus, for example, if the selected messenger RNA portion is the TAR region of HIV, then the oligonucleotide or oligonucleotide analog is constructed so as to mimic the TAR region sufficiently such that tat protein coded by another portion of the HIV messenger RNA is effectively complexed with or bound to the mimicking molecule. Similar considerations attend the preparation of oligonucleotide and oligonucleotide analog RNA mimics directed at the CAR and GAG-POL regions of HIV.

BRIEF DESCRIPTION OF THE DRAWINGS

FIG. 1A depicts the linear HIV-1 TAR element sequence. Underlined portions connote loops and bulges.

FIG. 1B depicts a computer-predicted secondary structure of the HIV-1 TAR element.

FIG. 2 sets forth the partial linear structure of the HIV-1 CAR RNA sequence corresponding to nucleotides 7357–7627.

DETAILED DESCRIPTION OF PREFERRED EMBODIMENTS

Figure 3:
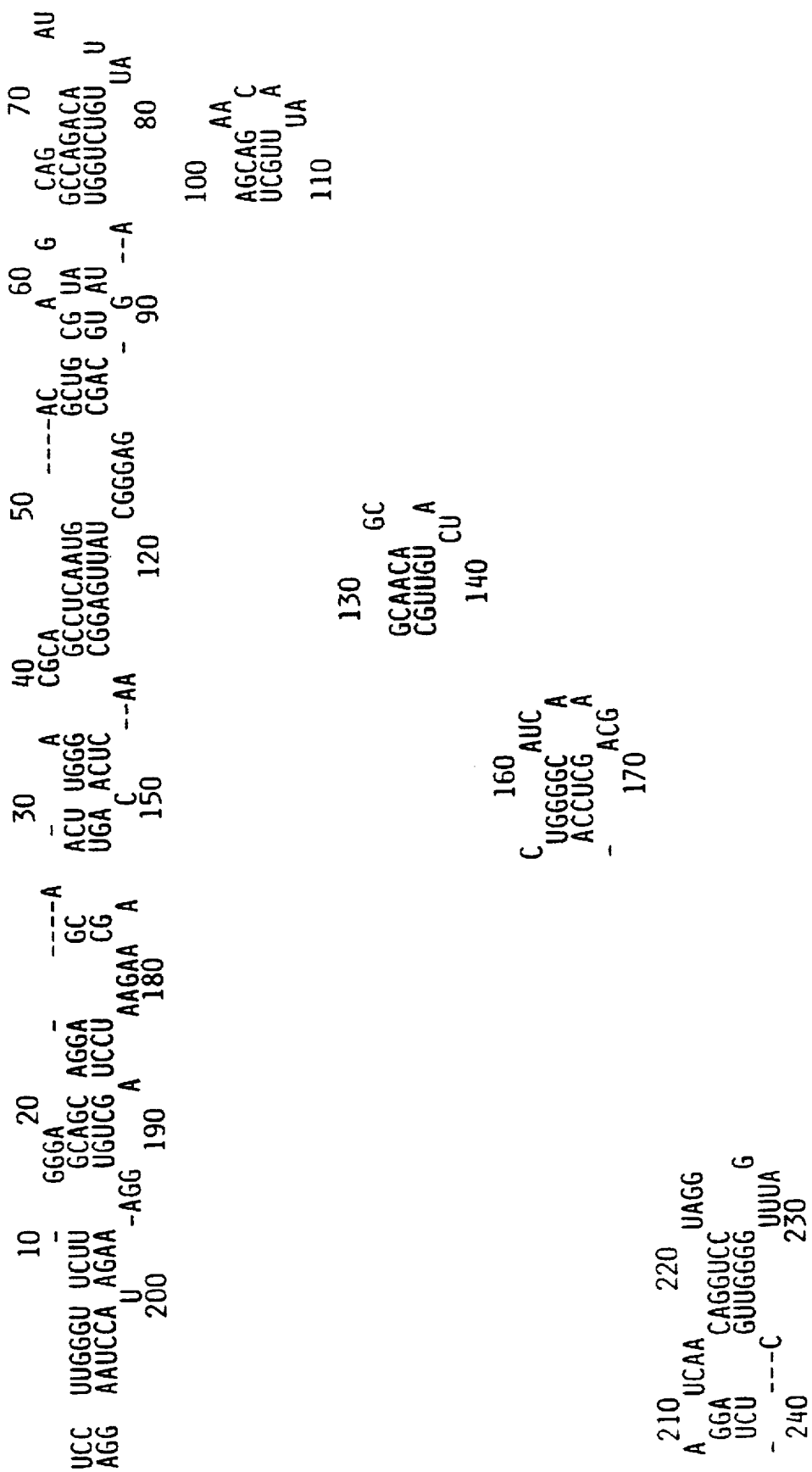
FIG. 3 shows a computer-predicted secondary structure of the HIV-1 CAR element
Figure 4:
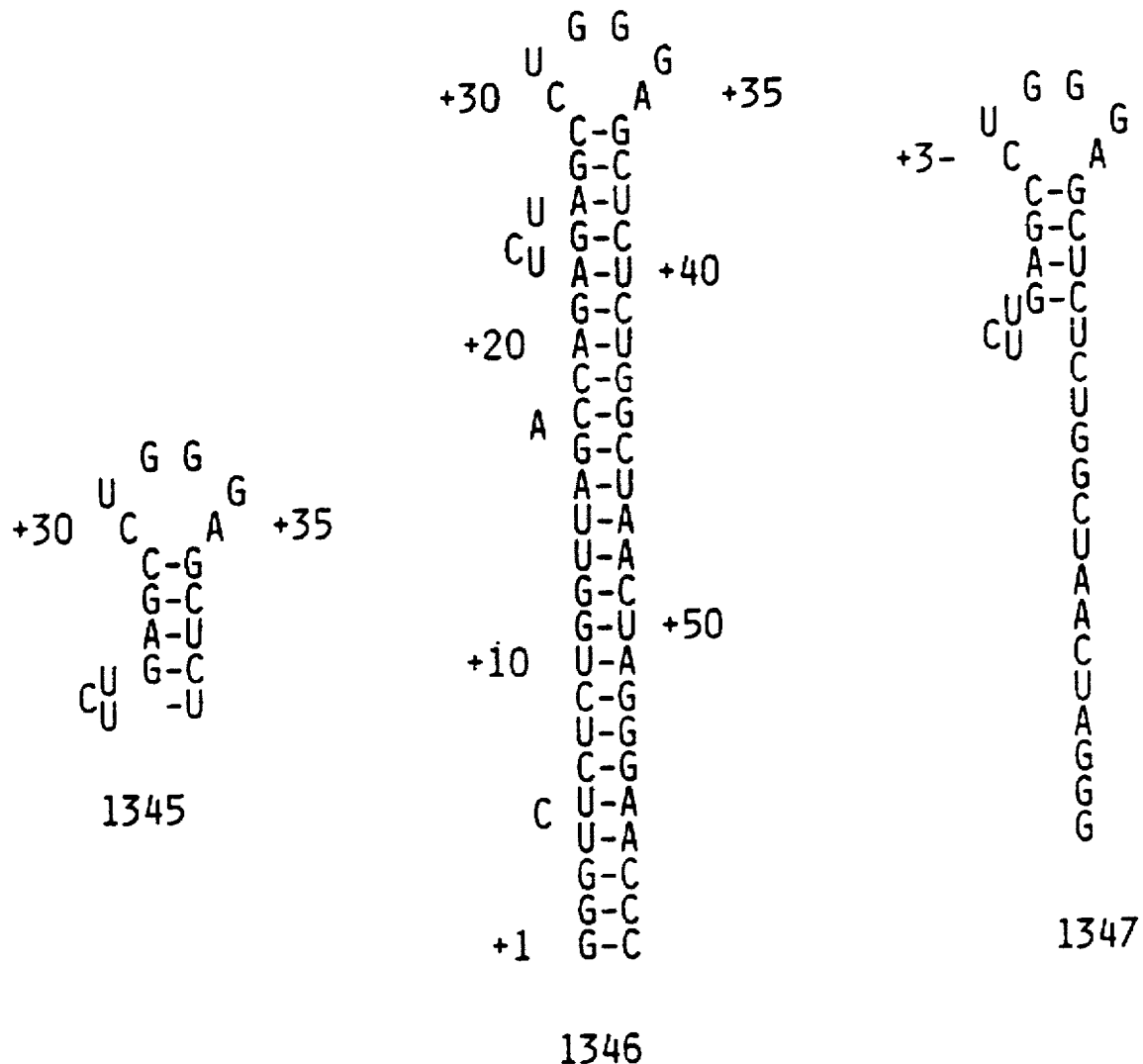
FIG. 4 shows the structure of oligonucleotides identified as 1345 (SEQ ID NO:14), 1346 (SEQ ID NO:15) and 1347 (SEQ ID NO:16).

In accordance with the present invention, compositions which mimic the structure of biological RNA molecules of significant importance are provided. The present invention employs oligonucleotides and oligonucleotide analogs to mimic the structures of the biological RNA molecules. In the context of this invention, the term "oligonucleotide" refers to a plurality of joined nucleotide units formed from naturally-occurring bases and cyclofuranosyl groups joined by native phosphodiester bonds. This term effectively refers to naturally-occurring species or synthetic species formed from naturally-occurring subunits.

"Oligonucleotide analog," as that term is used in connection with this invention, refers to moieties which function similarly to oligonucleotides but which have non-naturally occurring portions. Thus, oligonucleotide analogs may have altered sugar moieties or inter-sugar linkages. Exemplary among these are the phosphorothioate and other sulfur containing species which are known for use in the art. They may also comprise altered base units or other modifications consistent with the spirit of this invention.

In accordance with certain preferred embodiments, at least some of the phosphodiester bonds of the oligonucleotide have been substituted with a structure which functions to enhance the ability of the compositions to penetrate into the region of cells where the RNA whose activity is to be modulated is located. It is preferred that such linkages be sulfur-containing. It is presently preferred that such substitutions comprise phosphorothioate bonds. Others such as alkyl phosphothioate bonds, N-alkyl phosphoramidates, phosphorodithioates, alkyl phosphonates, and short chain alkyl or cycloalkyl structures may also be useful. In other preferred embodiments, the phosphodiester bonds are substituted with structures which are chiral and enantiomerically specific. In accordance with other preferred embodiments, the phosphodiester bonds are substituted with structures which are, at once, substantially non-ionic and non-chiral. Persons of ordinary skill in the art will be able to select other linkages for use in the practice of the invention.

It is generally preferred for use in some embodiments of this invention that the 2' position of the linking sugar moieties in at least some of the subunits of the oligonucleotides or oligonucleotide analogs be substituted. Thus, 2' substituents such as OH, SH, F, OCH$_3$, OCN, O(CH$_2$)$_n$CH$_3$ where n is from 1 to about 10 and other substituents having similar properties may be useful in some embodiments.

Oligonucleotide analogs may also include species which include at least some modified base forms. Thus, purines and pyrimidines other than those normally found in nature may be so employed. Similarly, modifications on the cyclofuranose portions of the nucleotide subunits may also occur as long as the essential tenets of this invention are adhered to.

Such analogs are best described as being functionally interchangeable with natural oligonucleotides (or synthesized oligonucleotides along natural lines), but which have one or more differences from natural structure. All such analogs are comprehended by this invention so long as they function effectively to mimic the structure of the desired RNA.

The oligonucleotides and oligonucleotide analogs in accordance with this invention preferably comprise from about 3 to about 100 subunits. It is preferred that such oligonucleotides and analogs comprise greater than about 6 subunits with from about 8 to about 60 subunits being more preferred, and still more preferred to have from about 10 to about 30 subunits. As will be appreciated, a subunit is a base and sugar combination suitably bound to adjacent subunits through phosphodiester or other bonds.

In vitro testing has shown potential therapeutic efficacy. Based on the results of such in vitro studies, it is believed that oligonucleotides and oligonucleotide analogs of this invention may be useful in diagnostics, therapeutics and as research reagents and kits. For therapeutic use, the oligonucleotide or oligonucleotide analog could be administered to an animal, especially a human, such as is suffering from a virus or retrovirus infection such as AIDS.

It is generally preferred to apply the therapeutic agent in accordance with this invention internally such as orally, intravenously or intramuscularly. Other forms of administration, such as transdermally, topically or intralesionally may also be useful. Inclusion in suppositories may also be useful. Use of the oligonucleotides and oligonucleotide analogs of this invention in prophylaxis is also likely to be useful. Use of pharmacologically acceptable carriers is also preferred for some embodiments. In accordance with the present invention, the oligonucleotides and oligonucleotide analogs which are useful in its performance are best described by the RNA which they are designed to mimic. Thus, it will be understood by persons of ordinary skill in the art that the oligonucleotides and analogs provided by this invention are those which are substantially identical to a portion of an RNA, especially a messenger RNA having a particular relationship to a diseased state. Thus, the RNAs which are to be mimicked in accordance with this invention are those RNAs having a secondary structure and which are capable of interacting with one or more proteins. While the present invention is not so limited, and while the inventors do not wish to be bound by any particular theory of operation of the present invention, it is believed that a number of regulatory centers are extant upon RNA coded by genes responsible for disease. It is believed that such regulatory RNA portions possess a secondary structure such as a hair pin loop, stem loop, bulge, or similar structure which is capable of interacting with a protein, generally a protein coded by a different portion of the same or different RNA. It is generally believed in some cases that the interaction of the protein or proteins with the regulatory RNA center causes or leads to an enhancement of translation of the RNA into protein. Overall, this is considered to be an enhancement in the expression of the underlying gene since, of course, the RNA is derived from said gene. The modulation of such enhancement is an object of this invention.

It is believed that preparation of mimics to these regulatory RNA portions and placement of quantities of such mimics, which are oligonucleotides or oligonucleotide analogs, into the cells or tissues which are suffering from infection, can result in a diminution of the infection; a modulation of expression of the underlying gene. This is believed to be effected by interaction of the protein or proteins with the mimic molecules such that interaction of the protein with the regulatory RNA portion is minimized. Accordingly, enhancement in the expression of the underlying gene is similarly modulated. The present invention is believed to be quite general in application. Thus, if an RNA is believed to be capable of interaction with a protein in a regulatory sense as discussed herein before, then design of an oligonucleotide or oligonucleotide analog which mimics the RNA or at least a portion thereof may lead to therapeutic materials and methods. Thus, by contacting an animal suffering from such infection with a mimicking oligonucleotide or oligonucleotide analog, diminution in the infection may be had.

While at present, the RNAs which are believed to have the regulatory relationship discussed above all appear to have secondary structures such as stem loops, bulges and the like, it is possible that regulatory RNA segments may exist which do not enjoy such secondary structures. In such case, the present invention is to be understood to contemplate the preparation of mimicking oligonucleotides or oligonucleotide analogs for such RNA as well. Similarly, this invention will be understood to extend to therapeutic methods and compositions for such RNAs.

A number of RNA secondary structures have recently been identified for which application of this invention will likely provide therapeutic utility. Some of these include the HIV TAR structures as reported by S. Feng, E. C. Holland, in *Nature* 334, 165 (1988); including the stem loops at nucleotide 5–54, and 58–104 according to the nucleotide sequence as described by Ratner in L. Ratner, W. Haseltine, R. Patarca, K. J. Livak, B. Starcich, S. F. Josephs, *Nature* 313, 277 (1985); the boundary between the EGP/OMP regions of HIV as disclosed by S. Le, J. Chen, M. J. Braun, M. A. Gonda, J. V. Maizel, in *Nucl. Acids Res.* 16, 5153 (1988); the boundary between the TMP/env genes of HIV (ibid); the HIV CAR structure as reported by E. T. Dayton, D. M. Powell, A. I. Dayton, in *Science* 246, 1625 (1989); and the stem loop structure at the junction between the HIV gag and pol genes (nucleotides 1629–1674); the HIV CRS element, and the human iron responsive element (IRE) as described by J. L. Casey, M. W. Hentze, D. M. Koeller, et al., in *Science* 240, 924 (1988). In addition, there are regions of RNA which are primarily thought of as single stranded areas which have been identified as sites for protein binding. For example, the sequence 5'-AUUUA-3' has been identified as a signal for a protein to bind which leads to degradation of RNA as disclosed by J. S. Malter, in *Science* 246, 664 (1989). The structure of this region is not known. However, that does not preclude the practice of this invention with this sequence. Additional RNA elements, with as yet unknown structures, can also be the subject of this invention.

It is not necessary to know the actual RNA structure in order to practice this invention, it is only necessary to know that a specific RNA sequence is recognized by an RNA binding protein and that this interaction has important biological consequences. In this regard, the viral RNA sequences and structures which are recognized by the structural proteins of retroviruses for virion formation are also the subject of this invention. The mimicry of any RNA structure which may interact with protein to effect an important biological function may fall within the spirit and scope of this invention.

The HIV TAR Element and Transactivation by the tat Protein

The HIV TAR element provides a good example of this invention. An elaborate set of control elements in the HIV genome determines whether the virus replicates or remains dormant. Of the nine genes identified in the HIV genome, only three are from the core and envelope as described by W. A. Haseltine, F. Wong-Staal, in *Scientific American*, 259:52 (1988). The other six genes are involved in regulation of the production of viral proteins.

Regulatory genes work by encoding a protein that interacts with a responsive element somewhere else on the viral genome. The major regulatory gens responsible for initiating the burst of replication is the tat (trans-activator) gens. The product of the tat gens, tat protein, works by interaction with a short sequence element known as TAR (trans-acting responsive element). The TAR sequence is encoded in the viral long terminal repeats (LTR's), and therefore is included in the mRNA from every HIV gens.

Expression of the tat protein results in increased expression of other HIV genes up to 1,000 fold, including the tat gens itself. Because of this autoregulatory positive feedback, and the fact that the TAR sequence is included in the mRNA from every HIV transcript, an immense amount of viral gens expression is triggered when the tat gens is activated. The interaction between the product of the tat gens and the TAR element is therefore crucial to the life cycle of HIV, and specific disruption of this interaction is believed likely to modulate gens expression, i.e., to interrupt the propagation of the virus..

The mechanism of trans-activation of TAR-containing genes by the tat protein has recently been studied intensely, as disclosed by P. A. Sharp, and R. A. Marciniak, in *Cell* 59, 229 (1989). It was found that tat increases the expression of TAR-containing genes by increasing both the amount of viral mRNA and the efficiency of its translation. Moreover, it appears that TAR functions as an RNA structure, rather than a DNA structure. The surprising result is that tat increases the transcription of TAR-containing genes, but does so by interacting with the TAR element in RNA. In order to achieve trans-activation, the TAR element must be located immediately "downstream" from the site of initiation of transcription. Moreover, TAR is orientation dependent; if inserted in the inverse orientation, it fails to function. TAR function does not depend upon the presence of other HIV sequences upstream of the initiation of transcription, but will act independently of the promoter.

Some of the strongest evidence that tat interacts with TAR as an RNA structure has come from mutagenesis experiments. Efforts to study the TAR element and RNA structure were stimulated by the observation that the tat protein from HIV-1 was capable of trans-activating vectors containing the TAR region of HIV-2, a different strain of virus, even though there is very little primary sequence homology in the TAR region between the two strains. See S. Feng, E. C. Holland, in *Nature* 334, 165 (1988). However, examination of the TAR sequence from HIV-1 and HIV-2 with computer programs that predict RNA secondary structure revealed the potential of RNA stem-loop structures, with a single stem-loop in the TAR region of HIV-1 and three stem-loop structures in HIV-2. Although the compositions and lengths of the stems were divergent, all four loops contained the pentanucleotide CUGGG. FIG. 1 depicts the linear sequence of the HIV-1 TAR region with the feature underlined. Mutagenesis experiments by Feng, ibid, revealed that each of the nucleotides present in the loop is essential for transactivation by tat, but that base substitutions in the stem were tolerated so long as the stem structure was maintained. FIG. 1A and 1B depict the linear (primary) and secondary structures of HIV-1 TAR.

Further evidence for the TAR structure function was obtained from experiments in which the sequences flanking the stem-loop structure were altered creating competing secondary structures in the RNA that were more stable than the natural TAR stem-loop. See Ben Berkhout, in *Cell* 59, 273 (1989). This was accomplished by introducing additional sequences into the TAR-containing RNA that were antisense to the 5' side of the stem-loop structure. Transactivation of the modified TAR structure was lost, suggesting that the TAR sequences alone are not sufficient for trans-activation, but that these sequences must fold up in the proper secondary structure to be active. It also suggests that antisense sequences to the TAR stem-loop are capable of disrupting the natural RNA structure.

Direct biochemical evidence for TAR stem-loop structure has also been obtained. The TAR RNA has been enzymatically synthesized in vitro and probed with enzymes which selectively cleave single stranded regions of RNA, but not duplex structures. The results of the cleavage patterns were consistent with the computer predicted RNA secondary structure.

Thus, it now appears that:
1. The HIV tat protein is responsible for triggering an enormous amount of viral gene expression;
2. This occurs by interaction with the TAR sequence which is incorporated into every HIV mRNA transcript;
3. The HIV TAR sequence functions as an RNA secondary structure; and
4. The correct TAR RNA secondary structure is essential for tat trans-activation.

Compounds have now been discovered which are believed to specifically mimic the TAR RNA structure and interfere with tat trans-activation. These oligonucleotide and oligonucleotide analog compounds will likely have activity as therapeutic agents for HIV infection.

It is intended that all strains of HIV fall within the spirit and scope of this invention. It will be realized that different strains of HIV will have different TAR sequences which will therefore fold into different structures. This invention can be practiced on alternative strains of HIV by changing the sequence of the oligonucleotide or oligonucleotide analog to mimic the structure of the alternative strain. Thus, this aspect of the invention relates to all such strains and to oligonucleotide mimics for each respective TAR region.

TAR and tat function have been studied by removing the genes from the HIV genome and studying them in cell lines in isolation. Vectors have been constructed to study the interactions between the tat protein and TAR element. The tat gene is expressed under the SV40 promoter. The TAR region is expressed from a separate plasmid fused to an easily assayed reporter gene such as the chloramphenicol acetyl transferase gene (CAT) or the placental alkaline phosphatase gene (PAP) as reported, for example, by S. Feng, E. C. Holland, in *Nature* 334, 165 (1988) and by P. Henthorn, P. Zervos, M. Raducha, H. Harris, T. Kadesch, in *Proc. Natl. Acad. Sci. USA* 85, 6342 (1988).

Enzymatic activity in cell culture models has been shown to be dependent upon both the presence of the essential elements of the TAR region and the presence of the tat protein. Pertinent reviews include P. A. Sharp, R. A. Marciniak, *Cell* 59, 229 (1989); Feng supra.; Michael F. Laspia, Andrew P. Rice, Michael B. Mathews, *Cell* 59, 283 (1989); J. A. Garcia, D. Harrich, E. Soultanakis, F. Wu, R. Mitsuyasu, R. B. Gaynor, *EMBO J.* 8, 765 (1989); and Ben Berkhout, *Cell* 59, 273 (1989). In essence, the vector system reconstitutes the events of tat-mediated TAR transactivation which occurs in HIV infected cells.

tat/TAR transactivation can be assayed by placing the human placental alkaline phosphatase gene (PAP) under the regulatory control of the HIV-1 LTR sequences, which contain enhancer, promoter, and TAR elements. A plasmid containing the HIV-1 LTR, pHIVCAT-0, as described by S. Feng, E. C. Holland, *Nature* 334, 165 (1988), contains HIV U3 in its entirety and R up through position +78 (a HindIII site). Digestion of this plasmid with a combination of HindIII and AatII releases the CAT cassette along with the SV40 sequences responsible for the processing of the RNA. A second plasmid, pSV2APAP, contains the PAP cassette with eukaryotic processing signals, under the transcriptional control of an SV40 promoter, as referenced by P. Henthorn, P. Zervos, M. Raducha, H. Harris, T. Kadesch, in *Proc. Natl. Acad. Scio USA* 85, 6342 (1988). The PAP cassette and processing sequences can be released from the plasmid by digestion with HindIII and AatII. A new plasmid, pHIVPAP, was created by ligating the HindIII/AatII fragment containing the HIV-1 LTR and vector sequences from pHIVCAT-0, to the HindIII/AatII PAP cassette from pSV2APAP.

It has been shown that pHIVCAT-0 is transactivated in the presence of a second plasmid, pcDEBtat, which expresses the tat coding region under the regulatory control of the SV40 promoter. However, no CAT activity is seen in the absence of co-transfection of pcDEBtat as disclosed by Feng. To test the activity of oligonucleotides and oligonucleotide analogs, pcDEBtat and pHIVPAP were co-transfected into HeLa cells using the calcium/phosphate method. 48 hours post-transfection cells were harvested and assayed for PAP activity as described by Henthorn et al. The effects of oligonucleotides and oligonucleotide analogs were determined by adding the compounds directly to the transfection mixture or by adding the compounds to the media at various times and concentrations following transfection, followed by PAP assay at, for example, 24–48 hours post-transfection.

Cells were treated with the following exemplary oligonucleotide and oligonucleotide analog sequences:

Modulation of HIV LTR gene expression, as monitored by PAP activity, was observed.

To be useful pharmacologically in the treatment of the previously described tat-mediated pathologies, TAR mimetics minimally must satisfy certain general structure/function criteria which are not adequately met by unmodified TAR RNA. The specific compositions of matter presented herein are designed to achieve the following goals. First and foremost, nuclease resistance (to RNAses and RNA active DNAses) must be conferred. Secondly, the minimal TAR fragment required for tat binding should be employed. Enhanced tat binding specificity and affinity, and therapeutic index, can be achieved by conformational stabilization of the preferred conformation of bound TAR. Finally, compositions could have enhanced affinity and specificity for tat by improvements on the natural chemical basis of specificity. A number of TAR mimetic oligonucleotide sequences have been prepared in accordance with the teachings of the invention as shown in Table 1:

TABLE 1

TAR MIMETIC OLIGONUCLEOTIDE SEQUENCES

| OLIGO | SEQUENCE |
|---|---|
| TAR 59-mer 1–59 | 5'-GGG UCU CUC UGG UUA GAC CAG AUC UGA GCC UGG GAG CUC UCU GGC UAA CUA GGG AAC CC-3', SEQ ID NO: 1 |
| U-DNA-TAR #1973 40-mer 11–50 | 5'-GGU UAG ACC AGA UCU GAG CCU GGG AGC UCU CUG GCU AAC U-3', SEQ ID NO: 2 |
| A: P=S TAR 59-mer 1–59 | 5'-GGG UCU CUC UGG UUA GAC CAG AUC UGA GCC UGG GAG CUC UCU GGC UAA CUA GGG AAC CC-3', SEQ ID NO: 1 |
| loopless ΔTAR #2002/#2246 23-mer 16–29 (–A17) +36–45 | 5'-GCC AGA UCU GAG C-3', SEQ ID NO: 3 5'-GCU CUC UGG C-3', SEQ ID NO. 4 |
| 5-BrU TAR 59-mer 1–59 | 5'-GGG UCU CUC UGG UUA GAC CAG AUC UGA GCC UGG GAG CUC UCU GGC UAA CUA GGG AAC CC-3', SEQ ID NO: 1 |
| 2'-OMe ΔTAR #2306 29-mer 16–45 (–A17) | 5'-GCC AGA UCU GAG CCU GGG AGC UCU CUG GC-3', SEQ ID NO: 5 |
| 2' OMe, P=S ΔTAR #2195 29-mer 16–45 (–A17) | 5'-GCC AGA UCU GAG CCU GGG AGC UCU CUG GC-3', SEQ ID NO: 5 |

5'-                                                                      -3'
GGGUCUCUCU GGUUAGACCA GAUCUGAGCC UGGGAGCUCU CUGGCUAACU
AGGGAACCC                                                SEQ ID NO: 1

5'-                                                        -3'
GGUUAGACCA GAUCUGAGCC UGGGAGCUCU CUGGCUAACU      SEQ ID NO: 2

5'-                  -3'
UCUGAGCCUG GGAGCUCUCU                             SEQ ID NO: 10

5'-                        -3'
CCAGAUCUGA GCCUGGGAGC UCUCUGG                     SEQ ID NO: 11

5'-           -3'
GAGCCUGGGA GCUC                                   SEQ ID NO: 12

5'-   -3'
CUGGGA                                            SEQ ID NO: 13

TABLE 1-continued

TAR MIMETIC OLIGONUCLEOTIDE SEQUENCES

| OLIGO | SEQUENCE |
|---|---|
| #1345<br>18-mer<br>23-40 | 5'-UCU GAG CCU GGG AGC UCU-3',<br>SEQ ID NO: 14 |
| #1346<br>58-mer<br>1-58 | 5'-GGG UCU CUC UGG UUA GAC CAG AUC UGA<br>GCC UGG G AGC UCU CUG GCU AAC UAG GGA<br>ACC SEQ ID NO: 15 |
| #1347<br>32-mer<br>23-54 | 5'-UCU GAG CCU GGG AGC UCU CUG GCU AAC<br>UAG GG-3', SEQ ID NO: 16 |
| #1348<br>17-mer<br>38-54 | 5'-UCU CUG GCU AAC UAG GG-3'<br>SEQ ID NO: 17 |
| #1349<br>25-mer<br>1-25 | 5'-GGG UCU CUC UGG UUA GAC CAG AUC U-3'<br>SEQ ID NO: 18 |

We have shown that the compound 2306, a 2'-O-methyl oligonucleotide analog comprising the sequence shown in Table 1, (SEQ ID NO: 5) has significant activity in inhibition of HIV gene expression.

Sullenger et al. disclose that expression of high levels of tRNA-TAR fusion transcripts correlated with effective inhibition of HIV-1 replication and prevented the cytopathic effects associated with HIV-1 replication in CEM SS cells. CEM SS is a human T-lymphoid cell line that is highly susceptible to HIV-1 replication. Sullenger et al. believe it is reasonable to assume that tat must physically associate with TAR in order to assert its function, whether binding directly or indirectly via a cellular factor. If so, overexpression of an RNA species encoding the TAR sequence could act as a decoy to bind tat and/or the cellular factor and prevent its binding to the TAR sequence encoded in the viral DNA. The result will be no activation of viral gene expression and no generation of progeny virus. TAR decoy-mediated inhibition of HIV-1 replication in CEM SS cells is shown to be very efficient. Base changes in the TAR stem or loop sequence which abolish tat-mediated trans-activation are also shown to abolish the ability of TAR decoy RNA to inhibit HIV replication in these cells. These results suggest but do not prove that HIV replication is inhibited in TAR decoy-containing cells because tat-mediated trans-activation is competitively squelched by the presence of an excess of nonviral TAR-containing RNA.

Graham et al., *Proc. Natl. Acad. Sci., USA* 87:5817-5821 (1990) disclose that a possible method of inhibiting tat-TAR interaction is to provide an excess of TAR decoys, i.e., TAR sequences (DNA or RNA) that competitively bind factors mediating transactivation and prevent them from acting. A problem in the use of TAR decoys may be the inability to put enough copies into a target cell to be effective. A suggested solution to this problem is to assemble many copies of the TAR in a head-to-tail tandem array and insert them as a single transcriptional unit, ideally behind a strong promoter. Graham et al. constructed an array of 12 TAR copies behind a strong promoter, the human β-actin promoter, and showed that the transcripts so produced in human cells do interfere with the tat-TAR interaction in vivo.

Although it has been shown that inhibition of HIV replication can be achieved without causing damage to cells, no one, until now, has been able to make an RNA therapeutic compound which can inhibit viral replication in vivo. In the present invention, RNA mimetics, with modifications conferring stability, are employed to maintain the TAR decoy function. These RNA mimics are distinct from the TAR decoys described by the prior art, which introduce DNA into the cell which is then transcribed into RNA in the cell; resulting RNA (TAR) has not been useful therapeutically because of its instability.

tat and Kaposi's Sarcoma

Kaposi's sarcoma (KS) is one of the diagnostic signs of AIDS, and is the initial manifestation in approximately 30% of patients with AIDS (Tom, *Hawaii Med. J.*, 48:131-134 (1989)). Skin lesions are the usual initial presentation, and can be single or multiple and range from faint pink to dark purple. The mucous membranes can be involved. In advanced disease, pain can be prominent; disfigurement and severe edema can also occur. Visceral involvement is also common in advanced disease; the tumors have been found in liver, spleen, gastrointestinal tract, oropharynx, conjunctiva, brain, testes, lungs, pancreas, aorta and heart. Kaposi's sarcomas are vascular tumors characterized by the proliferation of abnormal endothelial cells with spindle-shaped cells and extravasated red blood cells. Lesions in initial stages of disease are usually multifocal rather than metastatic. Metastases can occur, but usually late in the course of disease.

KS associated with AIDS differs from the previously known KS, which was rare and afflicted elderly men of Jewish or Mediterranean descent almost exclusively. This classic KS was usually indolent in its progression and required minimal treatment. In contrast, KS associated with AIDS is aggressive and is acknowledged as a significant cause of morbidity and mortality in AIDS patients. Treatment of AIDS-associated KS is largely experimental, nonspecific, and not very encouraging. Tom, *Hawaii Med. J.*, 48:131-134(1989) describes the disease in AIDS patients. The use of chemotherapy in these patients is controversial because it can further impair cellular immunity and increase the risk of opportunistic infections. Trials with single agents such as the vinca alkaloids, vincristine and vinblastine, and a podophyllotoxin, VP-16, have shown variable results and mild-to-moderate toxicity. However, response duration is short, and relapses frequent. Combination therapy has also been tried but is associated with a significant incidence of opportunistic infections. Immunotherapy has also been tried; alpha interferon has been shown to be active, however, this may be due to its antitumor effect. No treatment to date has resulted in any reversal of the underlying immune defect.

The tat protein, the product of one of the major regulatory genes of the AIDS virus, has been found to be a growth factor for cultured cells derived from Kaposi's sarcoma lesions of AIDS patients. These cells, called spindle cells (KS cells or KS spindle cells) are the suspected tumor cells of KS.

Salahuddin et al., *Science*, 242:430-433 (1988) disclose that AIDS-associated KS and possibly other types of KS may be initiated by signals that induce the growth of these KS cells. AIDS-KS cells cultured in the presence of conditioned medium from HTLV-II-infected and transformed T cell lines were studied. Growth stimulation was induced in the AIDS-KS cells, and not in control cells, suggesting that these KS spindle cells might play an important role in the development and maintenance of KS lesions and, more importantly, that a factor released by HTLV-infected and transformed T cell lines was responsible for stimulating the AIDS-KS cells.

Ensoli et al., *Nature*, 345:84-86 (1990) disclose that tat is released into the medium from both HIV-1-acutely infected H9 cells and COS-1 cells transfected with the tat gene. tat-containing medium specifically promoted growth of AIDS-KS cells (cultured spindle-like cells derived from KS lesions of AIDS patients) which was inhibited by anti-tat antibodies indicating that extracellular tat could be involved in the development or progression, or both, of KS in HIV-1-infected individuals. Transplantation of AIDS-KS cells into nude mice produced mouse lesions closely resembling KS.

The presence of KS-growth promoting activity in conditioned media from HIV-1-infected CD4+T cells, the absence of HIV-1 sequences in DNA from KS tissue or cultured cells, and the observation that transgenic mice carrying the tat gene develop KS-like lesions and express tat in the skin but not in the tumor cells, indicate that the role of HIV-1 in KS is indirect, and that tat itself might be released by infected cells and promote activation and growth of target cells involved in the formation of KS.

Further evidence for the role of tat in KS has resulted from experiments with transgenic mice. When the tat gene is introduced into mice, the gene is expressed in the skin only. The tat gene expression in the skin of transgenic mice is correlated with the development of skin tumors that closely resemble KS in humans.

Vogel et al., Nature, 335:606–611 (1988) disclose introducing the tat gene under the control of the HIV LTR into the germline of mice. The resulting transgenic animals developed dermal lesions resembling Kaposi's sarcoma (KS) suggesting that HIV, and specifically the tat gene product, contributes to the development of KS.

tat and Neurotoxicity

Infection with HIV-1 is often complicated by neurological syndromes that include dementia, subacute encephalitis, and vacuolar degeneration of the spinal cord. The identification and isolation of HIV-1 from the brain suggests that the retroviral infection is responsible for the neurological disorders observed in HIV-infected patients.

Sabatier et al., J. Virol., 65:961–967 (1991) disclose that the intracerebroventricular injection of tat or some tat fragments caused neurotoxic and lethal effects in mice. tat neurotoxicity was also investigated by structure-activity relationships, using binding experiments and electrophysiology. The tat binding site is identified as that region from 48 to 66 containing a highly basic domain critical for efficient tat trans-activation. It is shown that tat binds to the membrane-lipid bilayer of cell membrane by its basic domain. It is suggested that tat binding can directly provoke some biological effects such as neural stimulation, promoting neurological dysfunction.

tat and Immunodeficiency

One of the hallmarks of AIDS is depletion of T4 cells, with the subsequent development of immunodeficiency. However, destruction of CD4+T-cells does not adequately explain the immunopathogenic effects of HIV infection. For example, even early in infection, patient lymphocytes have a defect in their ability to recognize and respond to soluble antigens in vitro, even though there are still normal numbers of CD4+T lymphocytes. In contrast, ability of lymphocytes to proliferate in response to mitogens is not lost in these patients. Viscidi et al., Science, 246:1606–1608 (1989) disclose that tat inhibits antigen-induced, but not mitogen-induced, lymphocyte proliferation. In in vitro studies, 50 nM tat was sufficient for 50% inhibition, suggesting that tat may be a potent immunosuppressive agent. Viscidi et al. did not know whether tat must be provided extracellularly or whether tat produced internally can elicit these effects. In the present invention, topical application is believed to be most useful for treatment of KS. However, the form of administration will be dependent on the therapeutic utility.

Thus it has been shown that:

1. the tat protein and its interaction with TAR RNA is crucial for HIV replication,
2. tat protein secreted from cells appears to play a role in the development or progression of Kaposi's sarcoma in AIDS,
3. the tat protein has specific neurotoxic effects which suggest that binding of tat to membranes of the central nervous system may cause the neurological syndromes often associated with AIDS, and
4. the tat protein inhibits T-cell proliferation in a specific manner which indicates that tat might directly contribute to the immunosuppression associated with AIDS.

The HIV CAr Element and the rev Protein

The HIV CAR element provides another preferred embodiment of the invention. One of the regulatory events in the life cycle of the human immunodeficiency virus is accumulation of the large virion structural RNA's which are accumulated at the expense of the shorter, regulatory RNA's. In essence, the virus uses much of the same RNA material to encode each set of proteins. If the RNA's are more extensively spliced, the regulatory proteins are produced. If the RNA's are less extensively spliced, the structural proteins are produced. For example, See: W. A. Haseltine, F. Wong-Staal, Scientific American, 259:52 (1988). These events are regulated by a protein known as rev, which is produced by the rev gene. Rev's function is to enhance the transport of RNA from the nucleus of the cell to the cytoplasm. In the absence of rev, the mRNA's stay in the nucleus of the cell, where they are subject to splicing enzymes which convert them to mRNA's which encode regulatory proteins. In the presence of rev, the mRNA's are transported to the cytoplasm leading to less splicing.

Rev functions by binding to an RNA structural element known as the CAR element as reported by E. T. Dayton, D. M. Powell, A. I. Dayton, in Science 246, 1625 (1989). This structural element has also been referred to as the rre (rev-responsive element). The functional RNA has been localized to a 269 bp region in the env RNA with the coordinates 7358–7627. For example, See: L. Ratner, W. Haseltine, R. Patarca, K. J. Livak, B. Starcich, S. F. Josephs, Nature 313, 277 (1985). The linear CAR sequence is shown in FIG. 2. For convenience, this structure is referred to as the CAR element. The secondary structure of the CAR element is currently not known with certainty. However, it is possible to predict the secondary structure of the CAR element using computer programs commonly used by those skilled in the art such as the program of Zuker as described in M. Zuker, Science, 244, 48 (1989). The result of such an analysis yielded the result shown in FIG. 3. Each of the stem loop structures shown in FIG. 3 has the potential to interact with the rev gene product and each can be mimicked by oligonucleotides or oligonucleotide analogs as an embodiment of this invention. It is by no means certain that the structures predicted by the computer program and illustrated in FIG. 3 are correct. This does not restrict the practice of this invention for the CAR element structure, however. In this and all other cases where the actual RNA structure is uncertain, the invention can be practiced by preparing a series of oligonucleotides or oligonucleotide analogs which scan the sequence, beginning with the structures predicted to have the lowest energy according to the computer predictions, and proceed to make additional oligonucleotide or oligonucleotide analog compositions sequentially to the less energetically favored structures.

Assays to measure the normal function of the rev gene product can be conveniently performed according to published procedures. See Dayton et al., *J. Acq. Immune Deficiency Syndromes*, 1, 441, 1988. Briefly, vectors which express HIV mRNA in cells under regulatory control of a variety of promoters are transfected into cells along with a vector which expresses the rev protein. When rev functions normally to facilitate the transport of mRNA to the cytoplasm, the transported mRNA's encode the gag protein, which is detected by an immunoabsorbant assay. When oligonucleotides or oligonucleotide analogs interfere with this process, a decrease in production of gag protein is measured. The reagents needed to conduct these experiments are available from the National Institutes of Health through the AIDS Research and Reference Reagent Program, 1990 catalog, National Institute of Allergy and Infectious Diseases.

The effects of oligonucleotides and oligonucleotide analogs will be determined by adding the compounds directly to the transfection mixture or by adding the compounds to the media at various times and concentrations following transfection, followed by the assay at, for example, 24–48 hours post-transfection.

The present invention relates to compounds which are believed to specifically mimic HIV RNA structures and interfere with viral replication and function. These oligonucleotide and oligonucleotide analog compounds have been shown to have activity in modulating the expression of certain HIV proteins. In accordance with the teachings of the invention, the following examples are provided relating to oligonucleotide synthesis, purification and analysis, including specific oligonucleotide sequences and configurations; and cell-based evaluations of these exemplary oligonucleotides.

As shown in the following examples, therapeutically important RNA-binding proteins and sites on the RNA for target protein binding have been identified. RNA mimics have been made and chemically modified to improve pharmacokinetic properties, while preserving target protein binding properties. RNA mimics have been tested in a state-of-the-art cell culture model of the disease to demonstrate modulation of gene expression through RNA mimicry.

.EXAMPLES

Example 1
Oligonucleotide Synthesis and Purification
Synthesis
Unmodified oligonucleotides were synthesized on an Applied Biosystems 380B DNA Synthesizer using standard phosphoramidite chemistry with oxidation by iodine. The reagents, both CPG-bound and β-cyanoethyldiisopropyl-phosphites, were purchased from Applied Biosystems, Inc. (Foster City, Calif.). For preparation of phosphorothioate oligonucleotides, the standard oxidation bottle was replaced by 0.2M solution of 3 H-1,2-benzodithiole-3-one 1,1-dioxide (R. P. Iyer, W. Egan, J. B. Regan, and S. L. Beaucage, *J. Am. Chem. Soc.* (1990) 112:1253–1254) in acetonitrile for the stepwise thiation of the phosphoramidite linkages. The thiation cycle time was increased to 68 seconds. After cleavage from the CPG-column and deblocking in concentrated ammonium hydroxide at 55° C. (18 hours), the phosphorothioates were purified by trityl-on HPLC with a PRP-1 column using a gradient of acetonitrile in 50 mM of triethyl-ammonium acetate, pH 7 (4% to 32% in 30 minutes, flow rate of 1.5 ml/minute). Appropriate fractions were pooled, evaporated, and treated with 5% acetic acid at ambient temperature for 15 minutes. The solution was extracted with an equal volume of ethyl acetate, neutralized with ammonium hydroxide, frozen, and lyophilized. For the preparation of 2'-O-Me oligonucleotides, the normal phosphoramidite monomers were replaced with 2'-O-Me-substituted phosphoramidites purchased from Chemgenes. Analytical gel electrophoresis was accomplished in 20% acrylamide, 8M urea, 45 mM Tris-borate buffer, pH 7.40 V/cm.

NMR Analysis of Oligonucleotides
The relative amounts of phosphorothioate and phosphodiester linkages obtained by our synthesis were determined by $^{31}$P NMR spectroscopy. The spectra were acquired on a Varian NMR spectrometer with a $^{31}$P frequency of 162 MHz. Typically, 1,000 transients are coadded. A relaxation delay of 7.5 seconds between transients is used to insure a fully relaxed spectrum. The $^{31}$P spectra are acquired at ambient temperature using deuterium oxide or dimethyl sulfoxide-$d_6$ as a solvent. Phosphorothioate samples typically contained less than one percent of phosphodiester linkages.

Figure 5:
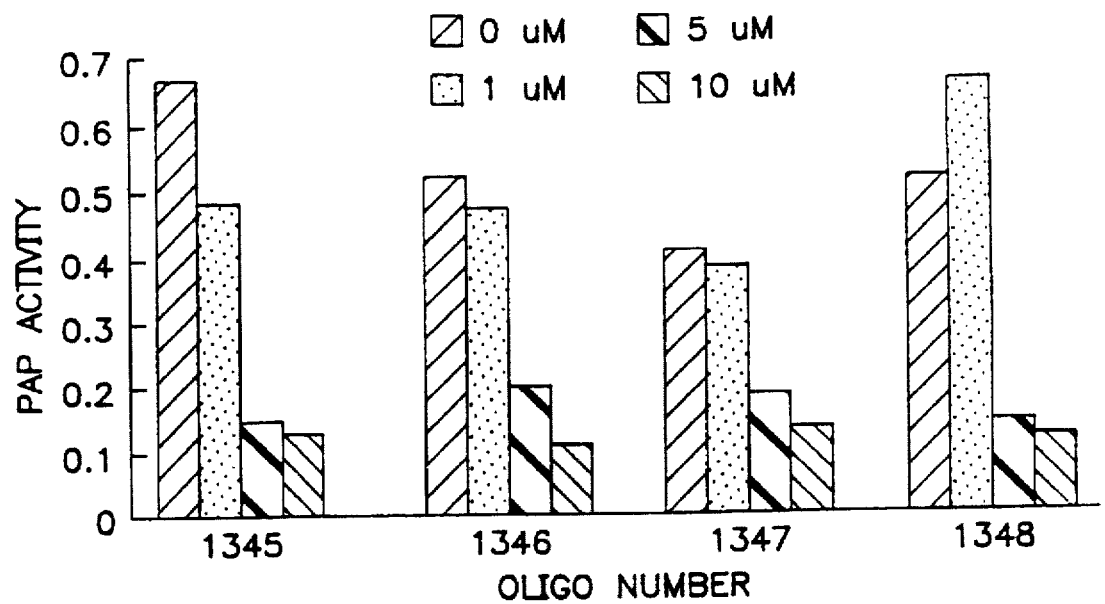
FIG. 5 is a graph showing the inhibition of HIV LTR gene expression observed with oligonucleotides 1345, 1346, 1347 and 1348.
Figure 6:
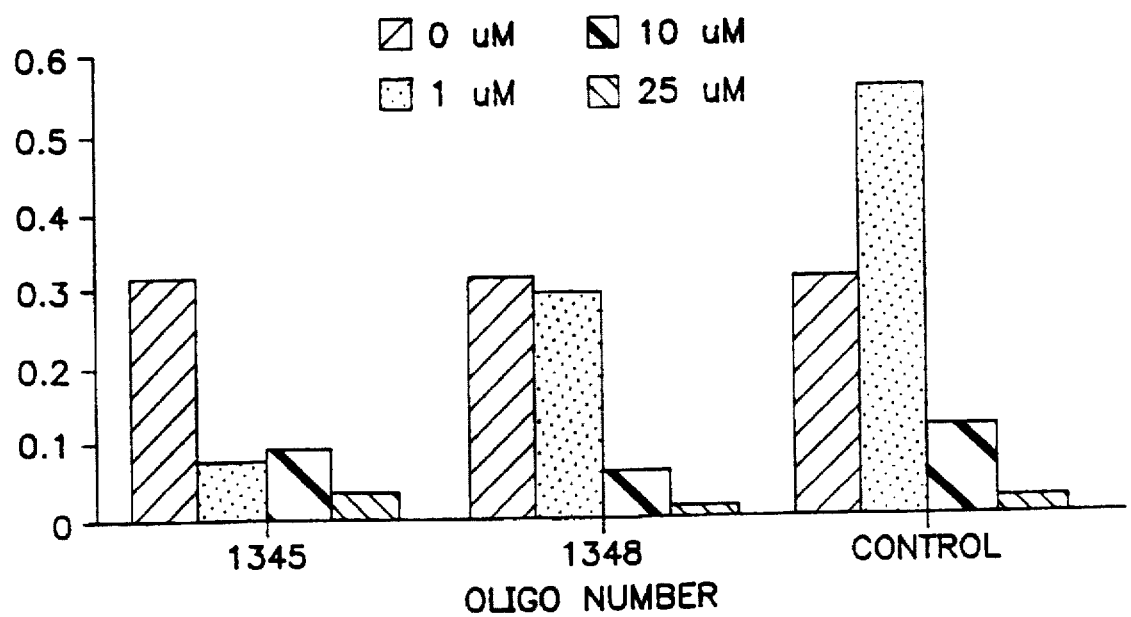
FIG. 6 is a graph showing the inhibition of HIV LTR gene expression observed with oligonucleotides 1345, 1349 and a control.

Example 2
Management of HIV LTR Gene Expression in Cells
HeLa cells were maintained in DMEM plus 10% FCS. For antisense experiments, cells were seeded in 6 well dishes at 50% confluency the day prior to the experiment. For each dish, 1 μg of pHIVpap and 12 μg of pcDEBtat were precipitated in 500 μl of 1× HBS and 32 μl of 2.5M CaCl$_2$. The CaPO$_4$ precipitate was then evenly divided between the six wells and allowed to sit for 6 hours prior to removal of the precipitate and addition of fresh media. Sixteen hours later, antisense oligonucleotides were transfected by the same method. The next day cells were washed 2× with TBS and harvested in 500 μl of which 100 μl were used in the protein assay. The remaining 400 μl of cell suspension was pelleted, then resuspended in 50 μl TBS buffer. Next, endogenous phosphatases were inactivated by heating to 65° C. for 30 minutes. The heat stable human placental alkaline phosphatase activity was then assayed by the addition of 500 μl of 5 mM PNPP (Sigma) in TEA buffer to the cell suspension, followed by incubation at 37° C. Phosphatase activity was determined at 30 minute intervals using 150 μl aliquots of the reaction mixture and measuring the absorbance at 405 nm with a Titertek Multiscan MCC/340 ELISA plate reader. The PAP activity was normalized to total protein in each well as determined by Bio-Rad protein assay, in which ⅓ of the harvested cells in TBS (0.1 μl) were added to 30 μl of Bio-Rad protein reagent, then incubated for 10 minutes at room temperature, followed by measurement of absorbance at 595 nm using the Titertek plate reader. The inhibition of PAP activity observed with oligonucleotides 1345 (SEQ ID NO: 14), 1346 (SEQ ID NO: 15), 1347 (SEQ ID NO: 16), 1348 (SEQ ID NO: 17) and 1349 (SEQ ID NO: 18) are shown in FIGS. 5 and 6.

Example 3
TAR RNA Synthesis
Template synthesis. A duplex DNA template for T7 RNA polymerase copying into TAR RNA was synthesized using the polymerase chain reaction (PCR). PCR primers were designed to be complementary to sequences of pHIV-PAP: the 5'-primer (36-mer) construction consisted of 5'-most sequences corresponding to the 17 base T7 RNA polymerase promoter, and were non-homologous to pHIV-PAP sequences, followed by 19 bases which were homologous to the first nucleotides of the TAR stem-loop (5'-AAT AGC ACT CAC TAT AGG GTC TCT CTG GTT AGA; SEQ ID NO: 6); the 3'-primer (20-mer) was homologous to the last 20 bases of the TAR stem-loop (5'-CCA GCA TGT CTG GAG GGC AG-3'; SEQ ID NO: 7). A standard PCR setup with Taq polymerase and 30 cycles of amplification was used. Amplified duplex template was purified by standard organic solvent extractions followed by ethanol/sodium acetate precipitation.

T7 RNA polymerase synthesis of TAR RNA. Duplex DNA template was added at 500 μM to a 1.0 mL reaction mix containing 1 2.5 mM each of GTP, CTP, ATP & UTP, 40 mM Tris-HCl pH 8.0, 1.0 mM spermidine, 5 mM DTT, 0.01% (v/v) Triton X-100, 20% (v/v) PEG 8000, 31 mM MgCl$_2$, and 10% (v/v addition previously optimized for polymerase reaction efficiency) of a T7 RNA polymerase preparation. The reaction was incubated for 4 h at 37° C. The RNA product was PAGE purified, dephosphorylated with calf intestinal alkaline phosphatase, concentration determined by UV absorbance, and 5'-end-labeled with $^{32}$P to high specific radioactivity (7000 Ci/mmol) using T4 polynucleotide kinase.

Example 4
Polyacrylamide Gel Mobility Shift Assays of TAR-tat Binding

All dilutions of [5'-$^{32}$P]-TAR RNA stock solution were made into TE, pH 7.5 containing 4 mg pdIdC (Boehringer Mannheim, Indianapolis, Ind.), and all dilutions of stock solutions (in water) of tat 37-mer peptide similarly were made into TE, pH 7.5 containing 500 nM BSA. Inclusion of pdIdC and BSA was made to reduce the effect of nonspecific adsorption (to solid surfaces) of dilute solutions of RNA and peptide, respectively, and independently were shown to be without effect on the specific binding of tat37 to TAR RNA. tat37 used was obtained from the UCSF Biotechnology Resource Core facility and was made by solid phase automated chemical synthesis, purified by RP HPLC, and characterized by amino acid analysis and mass spectrometry. TAR and analogs not made by T7 RNA polymerase synthesis were made by automated chemical oligonucleotide synthesis (indicated by synthesis number in Table 1). Gel mobility shift assays were performed by the addition of [5'-$^{32}$P]-TAR RNA and tat37 at indicated concentrations (Table 1) to a 10 μl reaction containing 10 mM Tris-HCl pH 7.5, 70 mM NaCl, 0.2 mM EDTA, 5% (v/v) glycerol, 500 nM BSA, and 4 mg pdIdC. Each binding mix was incubated for 30 min at 4° C. and then loaded directly onto a 10% (75:1 acrylamide:bisacrylamide) native PAG. Electrophoresis was performed using ½×TBE running buffer at 250V for about 2 hours at 43° C. Radiolabeled TAR RNA was then detected by autoradiography. For preliminary screening experiments, binding parameters were determined by visual estimation of relative intensities of exposure of film by free and specifically bound TAR and TAR mimetics/analogs, followed by appropriate mathematical and graphical analysis.

Further polyacrylamide gel mobility shift assays of TAR binding to tat 37 and tat 25 have been carried out. In some cases, a 25-amino acid tat peptide fragment, tat 25 (SEQ ID NO: 21), was used instead of the 37-amino acid tat 37 peptide (SEQ ID NO: 22). The results are shown in Tables 2 and 3.

TABLE 2

| | GEL MOBILITY-SHIFT tat-"TAR" BINDING ASSAYS | | | | | |
|---|---|---|---|---|---|---|
| OLIGO | [$^{32}$P-OLIGO] (pM) | [tat37] (nM) | 1:1 KD (nM) | $^x$REL (TAR 1:1 K$_D$) (OLIGO 1:1 K$_D$) | 2–3:1 KD (nM) | $^x$SITES (2:1 K$_D$/1:1 K$_D$) |
| TAR 59-mer 1–59 | 5–5000 | 10–500 | 40 | 1.0 | 200 | 5 |
| U-DNAΔTAR #1973 40mer 11–50 | 5 | 10–1000 | — | <0.001 | — | — |
| A:P = S TAR 59-mer 1–59 | 5 | 10–1000 | <10 | 4 | 30 | 3 |
| looplessΔTAR #2002/#2246 23-mer 16–29 (–A17) +36–45 | 5*/5000 no duplex 5000*/5 × 10$^6$ duplex | 10–1000 | — | <0.001 | — | — |
| 5-BrU TAR 59-mer 1–59 | 5 | 10–1000 | 40 | 1 | ND | ND |
| 2'-OMEΔTAR #2306 29-mer 16–45 (–A17) | 5–50 | 0.125–16.4 × 10$^3$ | 60–125 | 0.32–0.67 | 8.2 × 10$^3$ | 66 |
| 2'-OMe, P = SΔTAR #2195 29-mer 16–45 (–A17) | 5–50 | 0.125–16.4 × 10$^3$ | 4–10 | 4–10 | 8.0 × 10$^3$ 20 × 10$^3$ | 2–5 × 10$^3$ |

*When duplex structures are formed by intermolecular association and hybridization of individual oligos, rather than by intramolecular hybridization of a single oligo, then only one of the oligos is 5'-end-labeled with $^{32}$P and is distinguished from the unlabeled oligo by an *.

TABLE 3

GEL MOBILITY-SHIFT tat-"TAR" BINDING ASSAYS

| OLIGO | [$^{32}$P-OLIGO] (pM) | [tat25] (nM) | 1:1 KD (nM) | $^K$REL@ (TAR 1:1 K$_D$) (OLIGO 1:1 K$_D$) | 2:1 KD (nM) | $^K$SITES (2:1 K$_D$/1:1 K$_D$) |
|---|---|---|---|---|---|---|
| TAR 59-mer 1–59 | 50 | 0.01–10,000 | 0.01–0.1 | 1.0 | 10–100 | 1000 |
| ΔTAR29 #3153 16–45 (–A17) | 50 | 0.01–10,000 | 15–20 | 1.0 | — | — |
| 2'OMeΔTAR29 #2306 16–45 (–A17) | 50 | 0.01–10,000 | 10–100 | 0.15–2 | — | — |
| 2'OMe +2⁰ S29 non-TAR stem-3b bulge stem-6b loop #3220 | 50 | 0.01–10,000 | 5–10 | 1.5–4 | — | — |
| 2'OMe –2⁰ S29 non-TAR ss | 50 | 0.01–10,000 | — | — | — | — |
| 2'OMeΔTAR29 loopless +3 bp to upper stem #3223/#3250 16–32 (–A17) +c(33–35)–45 | 10,000*/ 10 × 10⁶ duplex | 0.01–10,000 | 300–1000 | 0.015–0.067 | — | — |
| 5-FdU23ΔTAR29 #3168 16–45 (–A17) | 50 | 0.01–10,000 | 10 | 1.5–2.0 | — | — |
| 6-AzaU23ΔTAR29 #3257 16–45 (–A17) | 50 | 0.01–10,000 | 10–20 | 0.75–2.0 | — | — |
| ΔTAR27 #3372 18–44 | 50 | 0.01–10,000 | ND | ND | — | — |
| ΔTAR35 #3410 13–47 | 50 | 0.01–10,000 | ND | ND | ND | ND |
| 2'-OMeΔTAR35 #13–47 | 50 | 0.01–10,000 | ND | ND | ND | ND |

*When duplex structures are formed by intermolecular association and hybridization of individual oligos, rather than by intramolecular hybridization of a single oligo, then only one of the oligos is 5'-end-labeled with $^{32}$P and is distinguished from the unlabeled oligo by a *
+indicates data presented are from finalized, complete, rigorous, optimized binding analysis
@For Tat25 binding data, all $^K$REL values are for "like vs like" sequences, i.e., the effect of a particular modification(s) is assessed only by direct comparison of identical sequences + or – (i.e., RNA) the modificiation, so that the only variable is the presence of absence of the modification(s).

Example 5
Development of Luciferase Assay for HIV Gene Expression pHIVluc is a plasmid which contains the luciferase gene under regulatory control of the HIV LTR. When this plasmid is present in the cell, it responds to the same regulatory signals which activate HIV gene expression by producing the enzyme luciferase. Luciferase can be easily assayed by adding a substrate, luciferin, under the appropriate conditions and measuring the amount of light produced in a luminometer. Thus, specific inhibition of luciferase production in cells is equivalent to inhibiting HIV gene expression, and is predictive of antiviral activity in humans. This assay is similar to that described by Felber B. K. and Pavlakis G. N. (Science, 239:184–187 (1988)), the major difference is simply the enzyme encoded by the reporter gene. To construct this plasmid, the plasmids pT3/T7 luc (Clonetech) and IP-RG-24 (a plasmid which contains the HIV LTR) were digested to completion with KpnI and HindIII. Restriction fragments containing the luciferase cDNA and the HIV LTR and other processing signals were isolated and ligated to generate pHIVluc, which expresses the luciferase protein under the control of the HIV LTR.

Example 6
Procedure for Measuring Inhibition of HIV Gene Expression in cultured Cells To test for inhibition of HIV gene expression, HeLa cells were seeded at 3×10⁵ cells per well of a 6 well plate 16 h prior to the experiment. Test compounds were added to triplicate wells at indicated concentrations. Following a 3 hour incubation the cells were calcium phosphate transfected with pHIVluc and pcDEBtat (Feng S. and Holland E. C., Nature, 334:165–167 (1988), which expresses tat, the HIV trans-activator protein. Briefly, 5 ug of pHIVluc and 6 ug of pcDEBtat were added to 500 ul of 250 mM CaCl$_2$, then 500 ul of 2× HBS were added followed by vortexing. After 30 minutes the DNA precipitate was divided evenly between the six wells of the plate, which was then incubated for 4–6 hours. The media and precipitate were then removed, the cells washed with PBS, and fresh media containing the test compound at the initial concentration was added and incubated for 16 hours.

Luciferase activity was then determined for each well as follows. Media was removed, then the cells washed 2× with PBS. The cells were then lysed on the plate with 200 ul of LB (1% Triton X-100, 25 mM glycylglycine pH 7.8, 15 mM MgSO$_4$, 4 mM EGTA, 1 mM DTT). A 75 ul aliquot from each well was added to 96 well plate along with 75 ul of assay buffer (25 mM glycylglycine pH 7.8, 15 mM MgSO$_4$, 4 mM EGTA, 15 mM KPO$_4$, 1 mM DTT, 2.5 mM ATP). The plate was then read in a Dynatec multiwell luminometer which injected 75 ul of Luciferin buffer (25 mM glycylglycine pH 7.8, 15 mM MgSO$_4$, 4 mM EGTA, 4 DTT, 1 mM luciferin) into each well and measured the light emitted.

Example 7
Activity of RNA Mimetics in Inhibition of HIV Gene Expression

Figure 7:
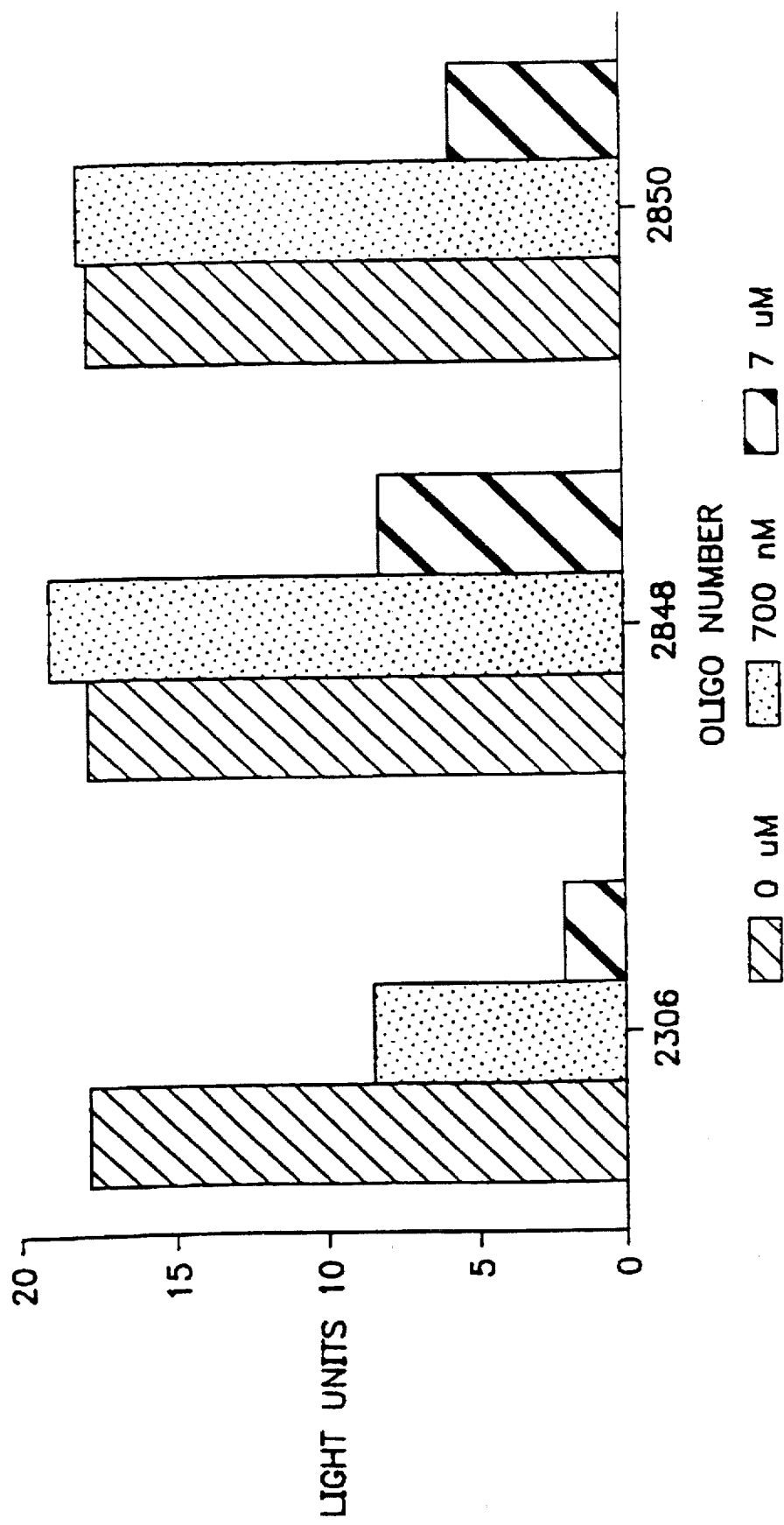
FIG. 7 shows the activity of oligonucleotides identified as 2306, 2848 and 2850 for inhibition of HIV LTR gene expression.

Compound 2306 (SEQ ID NO: 5) is a 2'-O-methyl oligonucleotide analog 29-mer which forms a truncated HIV TAR stem/loop structure. It was found that compound 2306 binds to the tat peptide in vitro. Compound 2848 (SEQ ID NO: 8) and 2850 (SEQ ID NO: 9) are also 2'-O-methyl analogs of similar length which form stem/loop structures, but are unable to bind tat peptide in vitro due to extensive mutations in the loop and bulge regions. In the HIV gene expression assay, compound 2306 shows significant activity in inhibition of HIV gene expression over the controls 2848 and 2850 compounds at doses below 1 μM (FIG. 7). At a higher dose (7 μM) there was some non-specific activity in the control compounds 2848 and 2850, which was less than the specific compound 2306.

Example 8
Binding of TAT to TAR Mimetic Analogs

Various nucleic acid analogs to TAR were assayed by the gel shift assay described in Example 4 for ability to bind the tat peptide. The binding activities of the various TAR mimetics are shown in Table 4.

TABLE 4

| ISIS # | Chemical Composition | tat (37) binding K$_a$ (nM) | Nuclease Resistance | Activity in Cells |
|---|---|---|---|---|
| 1973 | DNA with Uracils | >1000 | no | no |
| 2002 | RNA | >1000 | no | |
| 2306 | 2'-O-Me | 60 | yes | yes |
| 2195 | 2'-O-Me, PS | <10 | yes | |
| 3153 | RNA | 15–20 | no | |
| 2306 | 2'-O-Me | 10–100 | yes | yes |
| 3168 | RNA, 5FdU23 | 10 | no | |
| 3257 | 6-AzaUd23 | 10–20 | no | |
| 3220 | 2'-O-Me | 1–10 | yes | some |
| 3223/3250 | 2'-O-Me | 300–1000 | yes | |

The following diagram shows chemical modifications of TAR RNA which are functional as TAR mimetics:

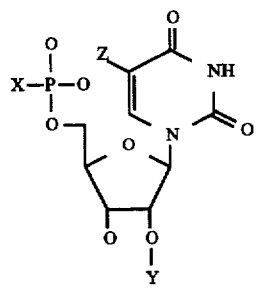

where,

X=S; Y=CH$_3$; and Z=Br, F, or H.

Example 9
Nuclease Stability of 21-O-ME vs 2'-Deoxy Oligonucleotides in HeLa Cell Nuclear Extract ISIS-2525, a 2'-O-Me RNA analog having the sequence AGC UCC CAG GCT (SEQ ID NO:19), and ISIS-2259, a deoxyoligonucleotide having the sequence AGC TCC CAG GCT (SEQ ID NO: 20) were compared for their resistance to nuclease digestion in HeLa cell nuclear extracts.

HeLa cell nuclear extract was prepared as follows: approximately 1.5×10$^7$ cells were washed in 20 ml PBS, (pH 7.4) and pelleted at 1500 rpm in a Beckman 17 rotor for 5 minutes at 4° C. Pelleted cells were resuspended in 5 ml 20 mM Tris-HCl (pH 7.2), 1 mM CaCl$_2$, 2 mM MgCl$_2$ and 0.5% NP40 and kept on ice for 15 minutes. Nuclei were pelleted at 2500 rpm in a Beckman 17 rotor for 5 minutes at 4° C. and the resulting nuclear pellet was resuspended in 1 ml PBS. Nuclei were resuspended and lysed using a Dounce homogenized following 20 strokes each of a loose and tight fitting pestle at 4° C.

To determine the rate of nuclease degradation of the oligonucleotides, oligonucleotide was added to HeLa cell nuclear extract to a final concentration of 66 μg/ml (approximately 10 μM). Following incubation at 37° C., 15 μl aliquots (containing 1 μg of oligonucleotide) were removed and added to 15 μl of a solution of 9M urea in 2×TBE. Aliquots were mixed and frozen at 20° C. until electrophoresis on 20% polyacrylamide/7M urea slab gels. Following electrophoresis, gels were stained using "Stains All" (Sigma Chem Co., St. Louis, Mo.). After destaining, gels were analyzed by laser densitometry using the UltraScan XL (Pharmacia LKB Biotechnology, Uppsala, Sweden).

Figure 8:
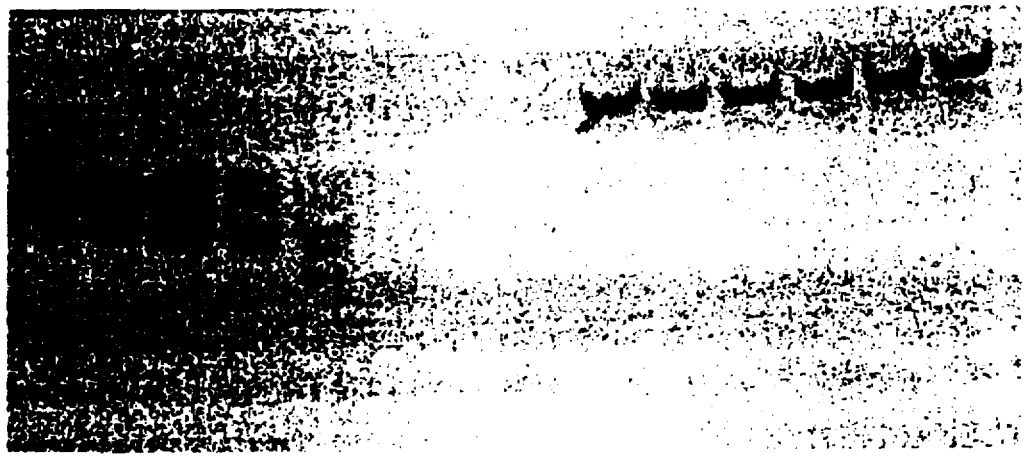
FIG. 8 is a pen and ink rendition of a stained gel showing that the 2'-deoxy sequences degrade over time in HeLa nuclear extract, whereas the 2'-O-Me sequences are resistant to nuclease degradation.

FIG. 8 is a photograph of a stained gel showing that the 2'-deoxy sequences degrade over time in HeLa nuclear extract, whereas the 2'-O-Me sequences are resistant to nuclease degradation.

Figure 9:
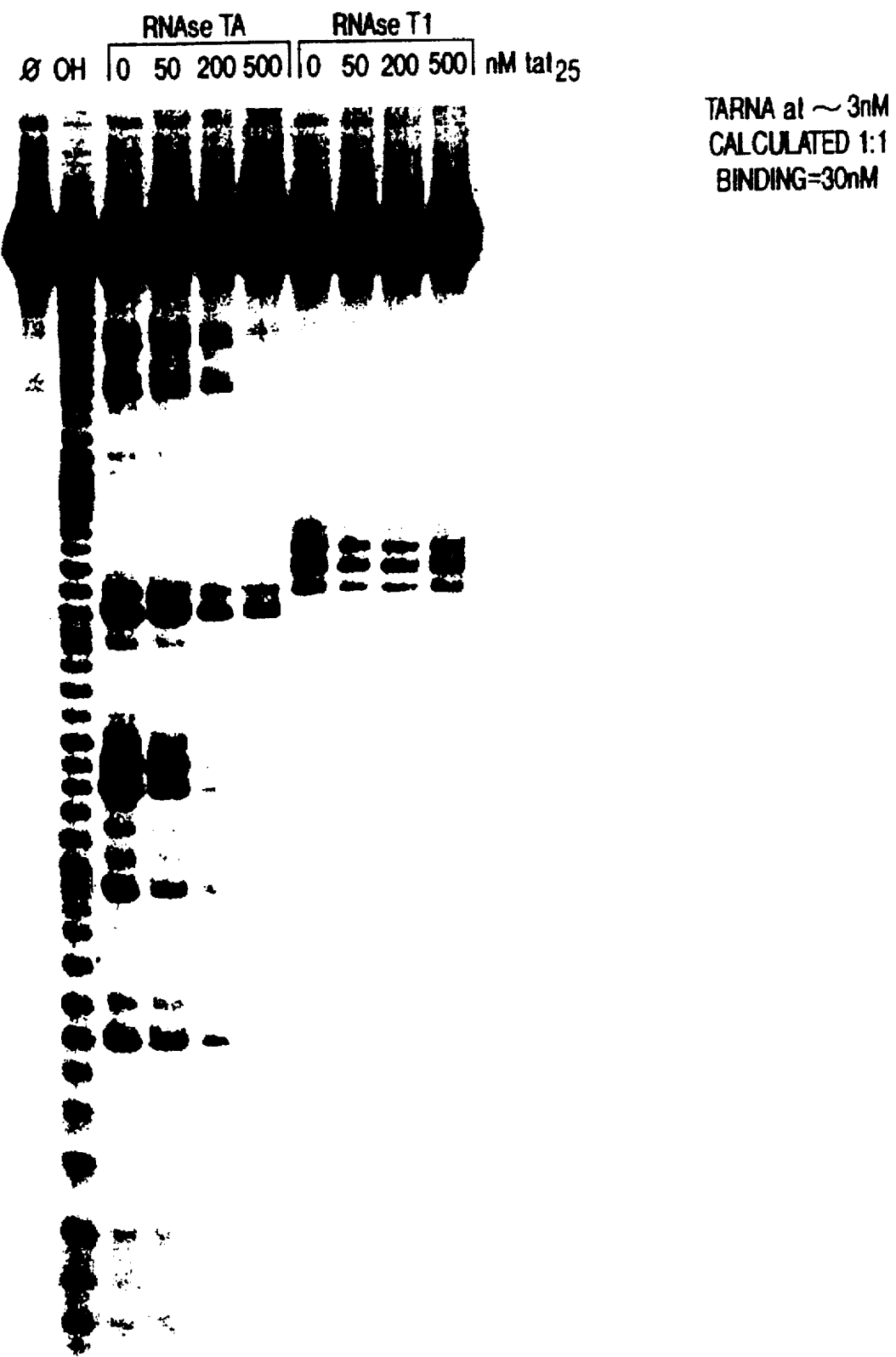
FIG. 9 is a pen and ink rendition of an autoradiograph showing % RNA cleavage in a determination of tat 25 peptide binding to TAR RNA.
Figure 10:
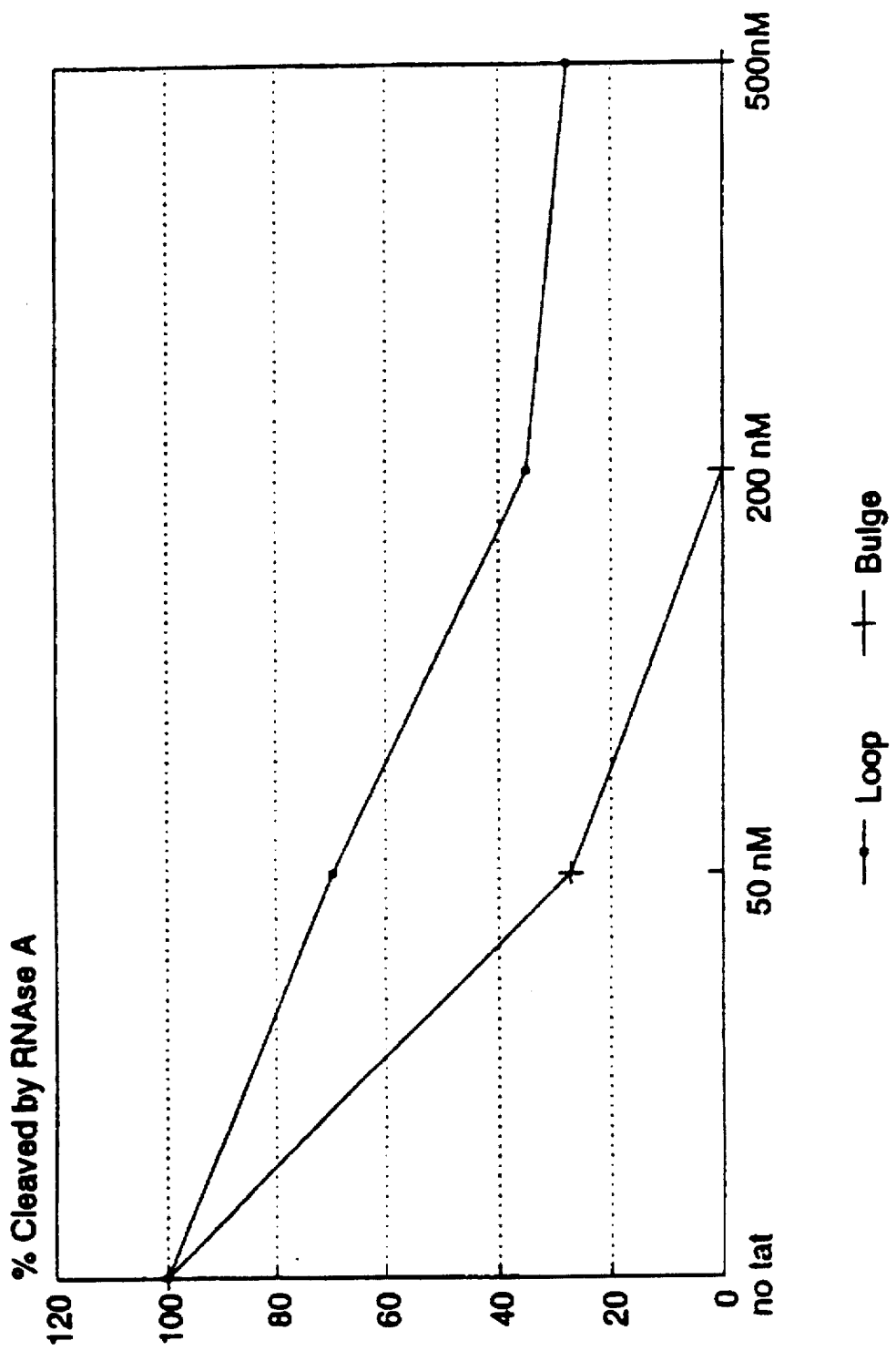
FIG. 10 is a graph showing % RNA cleavage in a determination of tat 25 peptide binding to TAR RNA.

Example 10
Determination of Site at which tat Peptide Binds to TAR RMA (tat Footprinting)

tat25 peptide was bound to 3 nM TAR RNA (end-labeled with $^{32}$P) in a buffer consisting of 10 mM Tris-HCl (pH 7.5), 70 mM NaCl, 0.5 mM EDTA, 5% glycerol at peptide concentrations of 0, 50, 200 and 500 nM. This tat/TAR mixture was incubated at 37° C. for 30 minutes. 10 μl aliquots were then taken from each reaction and treated with either RNAse A (a 10$^{-1}$ dilution of a 500 μg/ml stock solution), which specifically cleaves RNA at pyrimidine bases in single-stranded regions, or RNAse T1 (0.1 μM), which specifically cleaves RNA at guanine bases in single-stranded regions, for 3 minutes at room temperature. Reactions were stopped on ice, then an equal volume of 10M urea was added. The reaction products were resolved on a 12% acrylamide sequencing gel run at 30 W for 2 hours. The gel was dried and autoradiographed. Autoradiograms were scanned using a laser densitometer, and resulting decrease in band signal was graphed. The autoradiograph and graph showing %RNA cleavage are shown in FIGS. 9 and 10. RNAse degradation of the loop region of the TAR molecule occurs with both RNAse A or RNAse T1, but the bulge region is protected from degradation by RNAse A by tat peptide at concentrations of 200 nM and higher. This "footprint" indicates that tat is binding to the bulge region, protecting it from TNAse cleavage. This is shown graphically in the plot of percent of RNA (bulge or loop) cleaved vs increasing concentrations of tat.

What is claimed is:

1. A method for interfering in vitro with an essential viral function for replication of a Human Immunodeficiency Virus comprising contacting said virus or a medium or a cell containing said virus with an oligonucleotide or oligonucleotide analog comprising the sequence:

5'-CU GGG A-3'.

2. The method of claim 1 wherein said oligonucleotide or oligonucleotide analog further comprises, immediately 5' to the original sequence, at least a 3' portion of the sequence:

5'-UCU GAG C-3'.

3. The method of claim 1 wherein said oligonucleotide or oligonucleotide analog further comprises, immediately 3' to the original sequence, at least a 5' portion of the sequence:

5'-GC UC-3'.

4. The method of claim 1 wherein said oligonucleotide or oligonucleotide analog comprises a pyrimidine modified oligonucleotide.

5. The method of claim 1, wherein said oligonucleotide analog comprises oligonucleotide analog submits having improved nuclease resistance as compared with naturally occurring subunits.

6. A method for interfering in vitro with an essential viral function for replication of a Human Immunodeficiency Virus comprising contacting said virus or a medium or cell containing said virus with an oligonucleotide or oligonucleotide analog comprising the sequence:

5'-UCU GAG CCU GGG AGC UC-3' SEQ ID NO:14.

7. The method of claim 6 wherein said oligonucleotide or oligonucleotide analog further comprises, immediately 5' to the original sequence, at least a 3' portion of the sequence:

5'-CCAGA-3'.

8. The method of claim 6 wherein said oligonucleotide analog comprises oligonucleotide analog subunits having improved nuclease resistance as compared with naturally occurring subunits.

9. The method of claim 6 wherein said oligonucleotide or oligonucleotide analog comprises a pyrimidine modified oligonucleotide.

10. A method for interfering in vitro with an essential viral function for replication of a Human Immunodeficiency Virus comprising contacting said virus or a medium or a cell containing said virus with an oligonucleotide or oligonucleotide analog comprising from 6 to 50 nucleotides and a sequence selected from the group consisting of 5'-NNUCUNN-3',5'-NNUUUNN-3', and 5'-NNUUNN-3'.

11. The method of claim 10 wherein said oligonucleotide analog comprises a 2'-O-methyl analog.

12. The method of claim 10 wherein said oligonucleotide or oligonucleotide analog comprises SEQ ID NO:5.

13. The method of claim 12 wherein said oligonucleotide analog comprises modified bases having improved nuclease resistance as compared with naturally occurring bases.

14. The method of claim 12 wherein said oligonucleotide analog comprises a 2'-O-methyl analog.

* * * * *

UNITED STATES PATENT AND TRADEMARK OFFICE
CERTIFICATE OF CORRECTION

PATENT NO. : 5,736,294
DATED : April 7, 1998
INVENTOR(S) : Ecker, et al

Page 1 of 1

It is certified that error appears in the above-identified patent and that said Letters Patent is hereby corrected as shown below:

Column 14,
Line 20, "Car" should be --CAR--.

Column 23,
Line 47, "$10^{-1}$" should be --$10^{-7}$--.

Signed and Sealed this

Thirty-first Day of July, 2001

Attest:

*Nicholas P. Godici*

NICHOLAS P. GODICI
*Attesting Officer*  *Acting Director of the United States Patent and Trademark Office*